(12) United States Patent
Mundla et al.

(10) Patent No.: US 11,548,906 B2
(45) Date of Patent: *Jan. 10, 2023

(54) PROCESSES FOR THE PREPARATION OF SGLT-2 INHIBITORS, INTERMEDIATES THEREOF

(71) Applicant: EMMENNAR PHARMA PRIVATE LIMITED, Telangana (IN)

(72) Inventors: Maha Vishnu Mundla, Telangana (IN); Laxmi Narasimha Varaprasad Chintaginjala, Telangana (IN); Suresh Kumar Gunukula, Telangana (IN); Prabhakar Bellam, Telangana (IN)

(73) Assignee: Emmennar Pharma Private Limited, Hyderabad (IN)

( * ) Notice: Subject to any disclaimer, the term of this patent is extended or adjusted under 35 U.S.C. 154(b) by 157 days.

This patent is subject to a terminal disclaimer.

(21) Appl. No.: 16/876,659

(22) Filed: May 18, 2020

(65) Prior Publication Data

US 2020/0331946 A1 Oct. 22, 2020

Related U.S. Application Data

(63) Continuation-in-part of application No. 15/990,860, filed on May 29, 2018, now Pat. No. 10,703,772.

(51) Int. Cl.

| | | |
|---|---|---|
| *C07H 15/00* | (2006.01) | |
| *C07H 17/00* | (2006.01) | |
| *C07G 3/00* | (2006.01) | |
| *C07H 1/06* | (2006.01) | |
| *C07H 7/04* | (2006.01) | |

(52) U.S. Cl.
CPC ............ *C07H 1/06* (2013.01); *C07B 2200/13* (2013.01); *C07H 7/04* (2013.01)

(58) Field of Classification Search
None
See application file for complete search history.

(56) References Cited

U.S. PATENT DOCUMENTS

| 9,902,751 B2 | 2/2018 | Kaushik et al. |
| 2017/0247356 A1 | 8/2017 | Desai et al. |
| 2017/0319539 A1 | 11/2017 | Jetti et al. |
| 2018/0127391 A1 | 5/2018 | Bhirud et al. |

FOREIGN PATENT DOCUMENTS

| IN | 6139/CHE/2013 | 6/2016 |
| IN | 1790/MUM/2015 | 4/2017 |
| IN | 4286/MUM/2015 | 11/2017 |
| IN | 201621021804 | 12/2017 |
| IN | 201641022864 | 1/2018 |
| IN | 201741001520 | 7/2018 |

OTHER PUBLICATIONS

Xu et al. J. Med. Chem. (2014), vol. 57, pp. 1236-1251.*
Xu et al., "Design, Synthesis, and Biological Evaluation of Deuterated C-Aryl Glycoside as a Potent and Long-Acting Renal Sodium-Dependent Glucose Cotransporter 2 Inhibitor for the Treatment of Type 2", Journal of Medicinal Chemistry, (2014), 57, pp. 1236-1251.

* cited by examiner

*Primary Examiner* — Patrick T Lewis
(74) *Attorney, Agent, or Firm* — Carrier Blackman & Associates, P.C.; Joseph P. Carrier; Fulchand P. Shende

(57) ABSTRACT

The present invention relates to modified, improved processes for the preparation of sodium glucose co-transporter 2 (SGLT-2) inhibitors and intermediates thereof. More particularly, the present invention relates to improved processes for the preparation of gliflozin compounds such as empagliflozin and dapagliflozin, intermediates thereof. The product obtained from the processes of present invention may be amorphous or crystalline. Also, the products obtained from the present invention may be used for the preparation of medicaments for the prevention and/or treatment of diseases and conditions associated with SGLT-2 inhibition.

9 Claims, 3 Drawing Sheets

PROCESSES FOR THE PREPARATION OF SGLT-2 INHIBITORS, INTERMEDIATES THEREOF

CROSS-REFERENCE TO RELATED APPLICATIONS

This application is a Continuation-In-Part of U.S. patent application Ser. No. 15/990,860, filed May 29, 2018, which is based upon and claims the benefit of priority from Indian provisional patent application No. 201741018925, filed on May 30, 2017; Indian provisional patent application No. 201741043165, filed on Dec. 1, 2017; and Indian provisional patent application No. 201841017424, filed on May 9, 2018. The entire subject matter of these priority documents, including specification claims and drawings thereof, is incorporated by reference herein.

BACKGROUND OF THE INVENTION

1. Field of Invention

The present invention relates to novel, improved processes for the preparation of sodium glucose co-transporter 2 (SGLT-2) inhibitors. More particularly, the present invention relates to a novel, improved process for the preparation of gliflozin compounds such as empagliflozin and dapagliflozin, intermediates thereof. Also, the products obtained from the present invention may be used for the preparation of medicaments for the prevention and/or treatment of diseases and conditions in which SGLT-2 inhibitors are indicated.

2. Background of the Invention

Empagliflozin is a SGLT-2 inhibitor with a chemical name (1S)-1,5-anhydro-1-C-[4-chloro-3-[[4-[[(3S)-tetrahydro-3-furanyl]oxy]phenyl]methyl]phenyl]-D-glucitol and has the following structural formula:

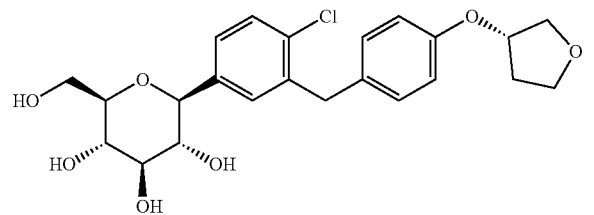 [SMILES: OC[C@H]1O[C@@H](c2ccc(Cl)c(Cc3ccc(O[C@H]4CCOC4)cc3)c2)[C@H](O)[C@@H](O)[C@@H]1O]

It was approved by the FDA in August, 2014 in the form of oral tablets for human use under the proprietary name, JARDIANCE® indicated as an adjunct to diet and exercise to improve glycemic control in adults with type 2 diabetes mellitus; and to reduce the risk of cardiovascular death in adult patients with type 2 diabetes mellitus and established cardiovascular disease.

Dapagliflozin is an orally active SGLT-2 inhibitor, approved by the FDA in January, 2014 in the form of oral tablets for human use under the proprietary name, FARXIGA®. The active ingredient of the approved product is chemically designated as (1S)-1,5-anhydro-1-C-[4-chloro-3-[(4-ethoxyphenyl)methyl] phenyl]-D-glucitol, (2S)-propylene glycol monohydrate and is marketed for the treatment of type 2 diabetes mellitus. The empirical formula is $C_{21}H_{25}ClO_6 \cdot C_3H_8O_2 \cdot H_2O$ and the molecular weight is 502.98. The structural formula is:

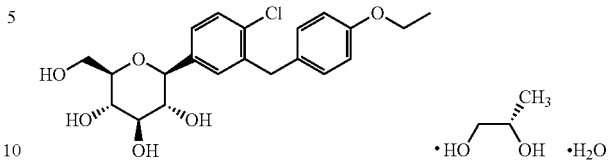

Several methods are known in the art for the synthesis of SGLT-2 inhibitors.

PCT publication No. WO 2005/092877 discloses glucopyranosyl-substituted benzene derivative, (1S)-1,5-anhydro-1-C-[4-chloro-3-[[4-[[(3S)-tetrahydro-3-furanyl]oxy]phenyl]methyl]phenyl]-D-glucitol (empagliflozin), and preparation process thereof, wherein 4-bromo-1-chloro-2-(4-methoxybenzyl)-benzene is reacted with boron tri-bromide ($BBr_3$) in dichloromethane to produce 4-(5-bromo-2-chloro-benzyl)-phenol which is reacted with t-butyl dimethyl silyl chloride in dichloromethane in the presence of triethylamine and N,N-dimethylaminopyridine to get [4-(5-bromo-2-chloro-benzyl)-phenoxy]-tert-butyldimethylsilane which is further reacted with n-butyllithium in tetrahydrofuran (THF) followed by condensation with 2,3,4,6-tetrakis-O-(trimethylsilyl)-D-glucopyranone. The resulting solution is reacted with methane sulfonic acid in methanol followed by reduction with triethylsilane and boron trifluoride etherate and acylated with acetic anhydride/pyridine in dichloromethane followed by treating with potassium hydroxide in methanol to produce phenolic intermediate. This phenolic intermediate is reacted with (R)-tetrahydrofuran-3-yl-4-methylbenzenesulfonate to produce empagliflozin.

The above process involves the use of hazardous boron tribromide as it reacts violently and decomposes to toxic compounds when on contact with moisture.

International patent application, WO/2017/130217 describes a process for preparing empagliflozin, wherein the process for preparing 4-bromo-1-chloro-2-(4-methoxybenzyl)benzene comprises reducing (5-bromo-2-chlorophenyl)(4-methoxy phenyl)methanone using titanium tetrachloride and triethylsilane. Further, (2R, 3R, triacetate is treated with (R)-tetrahydrofuran-3-yl 4-nitrobenzenesulfonate in DMF, followed by deprotection to yield empagliflozin.

Titanium tetrachloride ($TiCl_4$) is a strong Lewis acid, exothermically forming adducts with even weak bases such as THF and explosively with water and releasing HCl. (R)-tetrahydrofuran-3-yl-4-nitrobenzenesulfonate is not commercially available and its synthesis requires use of expensive starting materials, thereby increasing the raw material cost. This process may not be useful for economic production of empagliflozin.

International patent application, WO/2017/203457 discloses a process for preparing empagliflozin comprising reacting (R)-tetrahydrofuran-3-yl-4-methyl benzenesulfonate with (2S,3R,4R,5S,6R)-2-(4-chloro-3-(4-hydroxybenzyl)phenyl)-6-(hydroxymethyl)tetrahydro-2H-pyran-3,4,5-triol to yield empagliflozin.

However, the process for preparing compound (4-(2-chloro-5-iodobenzyl) phenoxy)(tert-butyl)dimethylsilane, involves multiple steps and makes use of expensive reagents such as 1,1,3,3-tetramethyldisiloxane (TMDS), tert-butyldimethylsilyl chloride (TBDMSCl) and use of cesium carbonate in preparing empagliflozin, thereby making it uneconomical.

U.S. Pat. Nos. 6,515,117; 7,375,213; 7,932,379; and 7,919,598 disclose processes for the preparation of dapagliflozin comprising the step of hydrolyzing an acetylated dapagliflozin, in the presence of an alkali metal hydroxide such as lithium hydroxide or sodium hydroxide to give pure dapagliflozin as an amorphous glassy off-white solid with a purity of 94%.

Inefficiencies known in the art for preparing SGLT-2 inhibitors include (1) a lack of stereo selectivity during formation of the desired β-anomer of the C-arylglucoside, (2) relatively long synthetic routes (linear syntheses), (3) uneconomic protection of hydroxyl groups, (4) use of hazardous reagents, and/or (5) complex work-up procedures and (6) use of expensive raw materials.

Hence, there exists a continuous need for alternate, improved, safe and cost effective synthetic routes for the preparation of SGLT-2 inhibitors, with high chemical and enantiomeric purity, applicable for large scale production.

The present inventors surprisingly found modified, improved processes for the preparation of SGLT-2 inhibitors particularly empagliflozin and dapagliflozin, which are cost effective, non-hazardous, less cumbersome, advantageous over prior art, involving simplified work-up procedures with high yields, better enantiomeric purity and are commercially scalable in industry.

SUMMARY OF THE INVENTION

The present invention provides novel, improved processes for the preparation of SGLT-2 inhibitors, preferably gliflozins, namely empagliflozin and dapagliflozin, intermediates thereof.

In one embodiment, the present invention provides a modified, improved process for the preparation of (1S)-1,5-anhydro-1-C-[4-chloro-3-[[4-[[(3S)-tetrahydro-3-furanyl]oxy]phenyl]methyl]phenyl]-D-glucitol i.e., empagliflozin, comprising reacting a compound of formula (7) in a suitable solvent with compound (8) in the presence of a base and optionally a phase transfer catalyst, as given below:

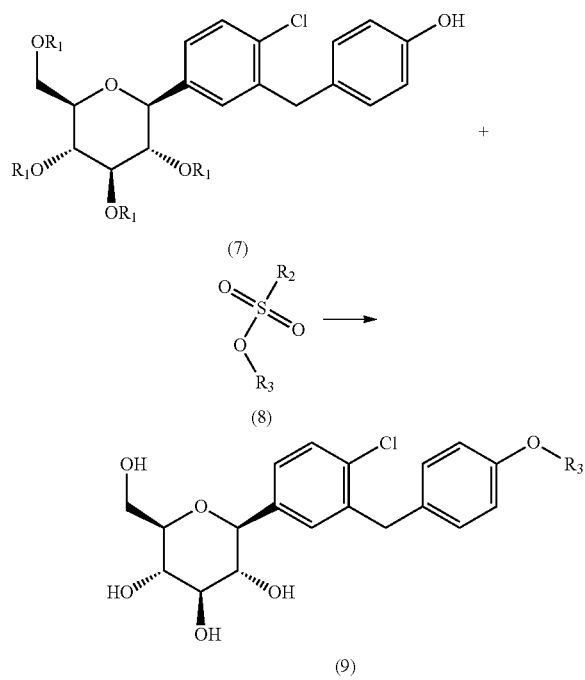

Wherein $R_1$ is hydrogen or a hydroxyl protecting group; $R_2$ is trifluoromethyl, $C_{1-6}$ alkyl, or an aryl group optionally substituted at para position with groups such as halogen, $C_{1-6}$ alkyl; and $R_3$ is tetrahydrofuran-3-yl.

In a second embodiment, the present invention provides a modified, improved process for preparing (1S)-1,5-anhydro-1-C-[4-chloro-3-[(4-ethoxyphenyl)methyl] phenyl]-D-glucitol i.e., Dapagliflozin, solvates or hydrates thereof, comprising reacting a compound (7) in a suitable solvent with compound (8) in the presence of a base and optionally a phase transfer catalyst, as given below:

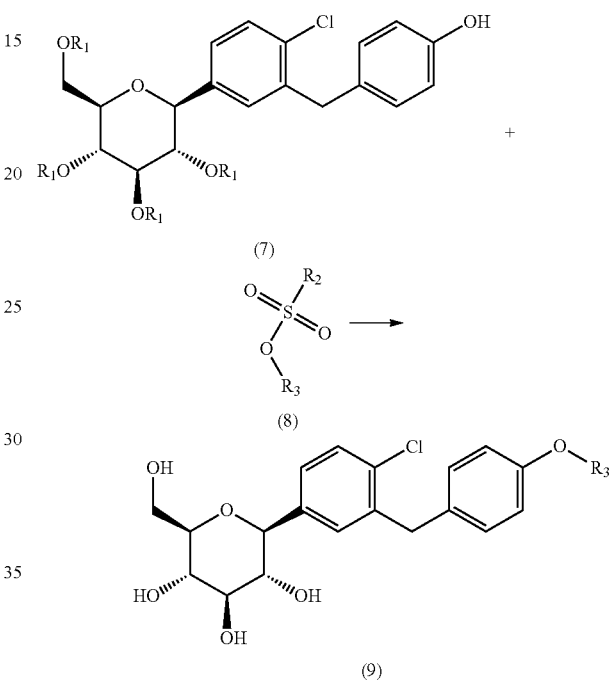

Wherein $R_1$ is hydrogen or a hydroxyl protecting group; $R_2$ is trifluoromethyl, $C_{1-6}$ alkyl, or an aryl group optionally substituted at para position with groups such as halogen, $C_{1-6}$ alkyl; and $R_3$ is ethyl.

In the above embodiments, the hydroxyl protecting group is selected from —C(O)OC$_1$-C$_6$ alkyl, optionally substituted —C(O)OC$_1$-C$_6$ aryl, optionally substituted —C$_1$-C$_{12}$ aryl (C1-C$_3$)alkyl, optionally substituted C$_7$-C$_{11}$ aryl carbonyl, —C(O)C$_1$-C$_6$ alkyl, C$_1$-C$_6$ alkylsulfonyl and silyl protecting groups.

In a third embodiment, the present invention provides a process for preparing crystalline form of empagliflozin, comprising: a) dissolving empagliflozin in a solvent or a mixture of solvents; b) heating and stirring the reaction mixture to a temperature up to 60±5° C. to form a clear solution; c) cooling the reaction mixture to 0-5° C.; d) filtering the solution, followed by drying under vacuum to provide crystalline empagliflozin.

In a fourth embodiment, the improved processes of the present invention provide crystalline empagliflozin characterized by a purity of about 99% or more by HPLC, stable for 6 months when stored at a temperature of 40±2° C. and 75±5% relative humidity (RH).

In a fifth embodiment, the improved processes of the present invention provide crystalline empagliflozin characterized by a purity of about 99% or more by HPLC, stable for 6 months when stored at a temperature of 25±2° C. and 60±5% relative humidity (RH).

DETAILED DESCRIPTION OF THE INVENTION

Figure 1:
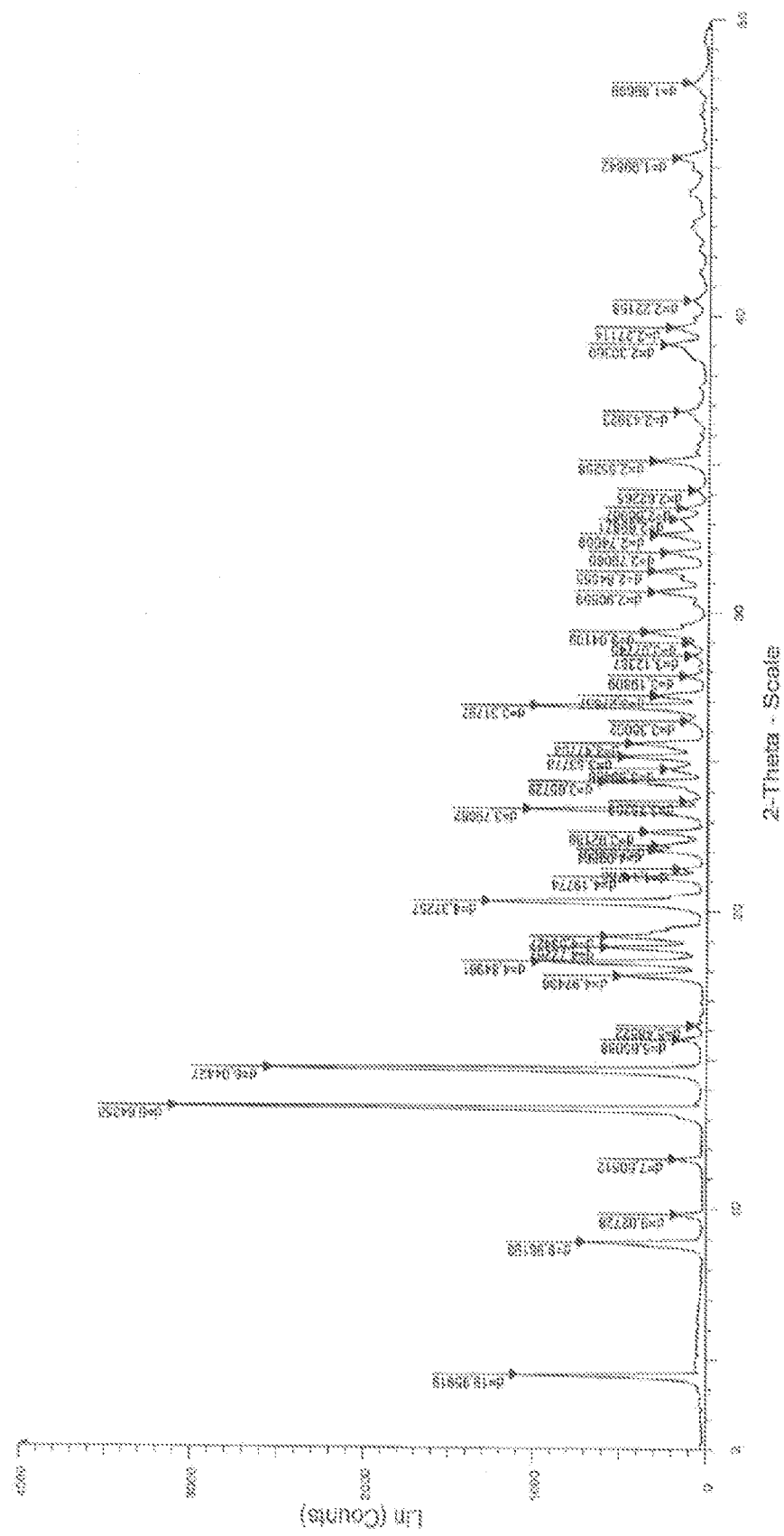
FIG. 1 represents powder X-ray diffraction pattern of crystalline Empagliflozin.
Figure 2:
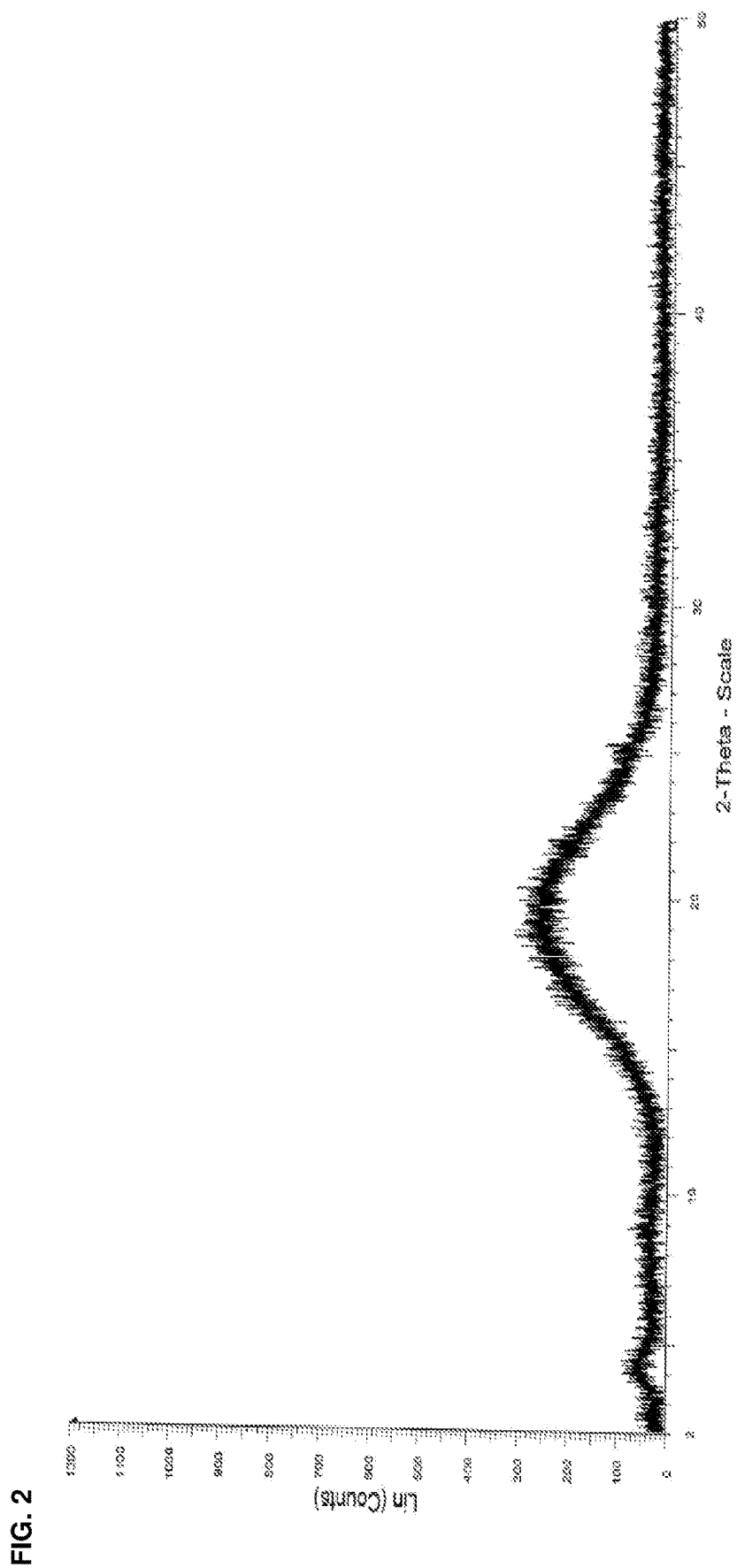
FIG. 2 represents powder X-ray diffraction pattern of amorphous Empagliflozin.
Figure 3:
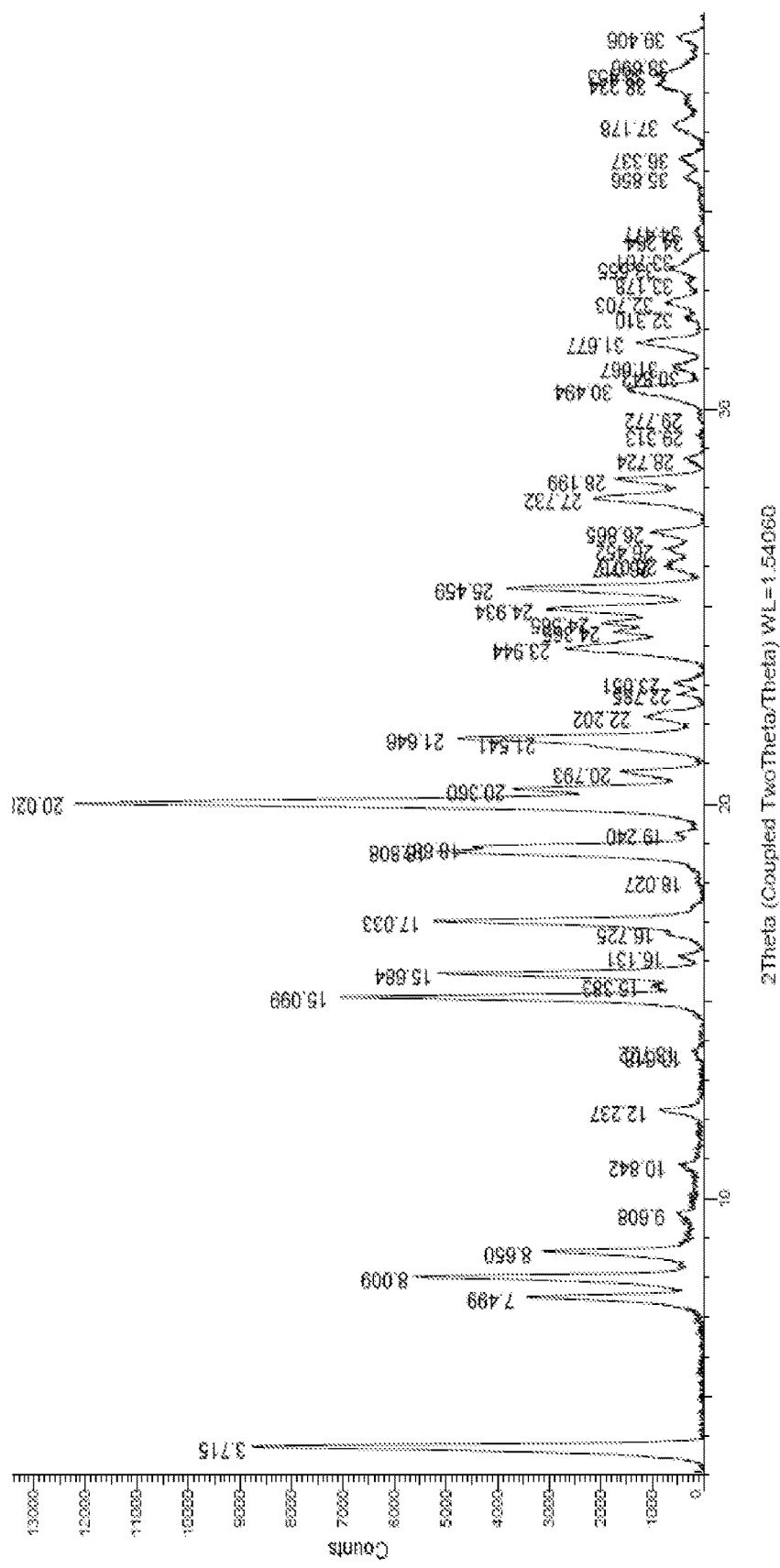
FIG. 3 represents powder X-ray diffraction pattern of crystalline Dapagliflozin propane-1,2-diol.

The present inventors have surprisingly found modified, improved cost-effective processes for preparing SGLT-2 inhibitors, particularly empagliflozin, dapagliflozin and intermediates thereof, which are commercially scalable with high enantiomeric purity and better yields with low technical expenditure.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, the term "SGLT-2" refers to sodium glucose co-transporter 2, which is a sodium dependent glucose transport protein. SGLT-2 is the primary co-transporter involved in renal glucose reabsorption. As used herein, "SGLT-2 inhibitor" refers to any molecule that can modulate SGLT-2 activity in vitro or in vivo.

The term "medicament" as used herein refers to a pharmaceutical composition containing the SGLT-2 inhibitor compounds prepared by the present invention, wherein the pharmaceutical composition may be used for human or non-human therapy of various diseases or disorders in a therapeutically effective dose.

The term "treatment" as used herein is defined as the management and care of a patient, e.g. a mammal, a human, for combating the disease, condition or disorder and includes the administration of SGLT-2 inhibitors to prevent the onset of the symptoms or complications or alleviating the symptoms or complications or eliminating the disease, condition or disorder.

As used herein, the term "protecting group" refers to a compound that is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry [See e.g. Greene's Protective Groups in Organic Synthesis by T. W. Greene and P. G. M. Wuts, 4th Edition; John Wiley & Sons, New York (2007)].

The terms such as "about", "substantially," and the like are to be construed as modifying a term or value such that it is not an absolute. Such terms will be defined by the circumstances and the terms that they modify as those terms are understood by those skilled in the art. This includes, at very least, the degree of expected experimental error, technique error and instrument error for a given technique used to measure a value.

In a first embodiment, the present invention provides a modified, improved process for the preparation of (1S)-1,5-anhydro-1-C-[4-chloro-3-[[4-[[(3S)-tetrahydro-3-furanyl]oxy]phenyl]methyl]phenyl]-D-glucitol i.e., empagliflozin, comprising reacting a compound of formula (7) in a suitable solvent with compound (8) in the presence of a base and optionally a phase transfer catalyst, as given below:

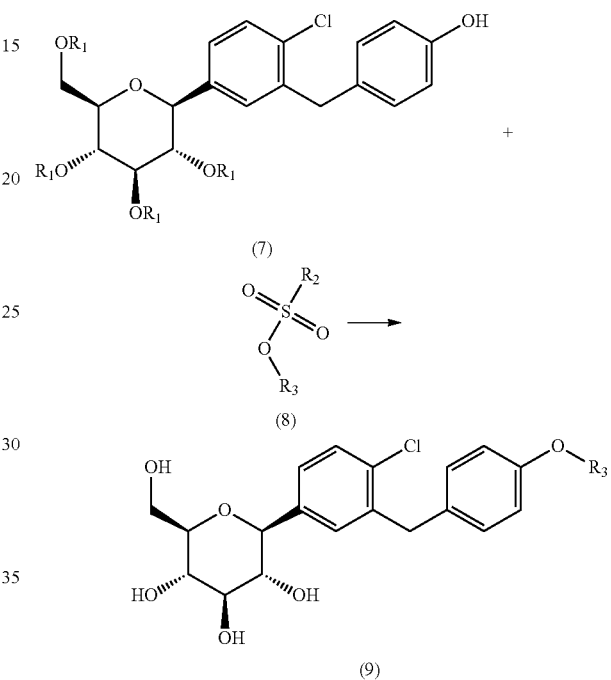

Wherein $R_1$ is hydrogen or a hydroxyl protecting group selected from —C(O)OC$_1$-C$_6$ alkyl, optionally substituted —C(O)C$_1$-C$_6$ aryl, optionally substituted —C$_1$-C$_{12}$ aryl(C$_1$-C$_3$)alkyl, optionally substituted C$_7$-C$_{11}$ aryl carbonyl, —C(O)C$_1$-C$_6$ alkyl, C$_1$-C$_6$ alkylsulfonyl; $R_2$ is trifluoromethyl, C$_{1-6}$ alkyl, or an aryl group optionally substituted at para position with groups such as halogen, C$_{1-6}$ alkyl; and $R_3$ is tetrahydrofuran-3-yl. In one preferred embodiment, $R_2$ is an aryl group, preferably phenyl. In another embodiment, $R_2$ is phenyl substituted with a C$_{1-6}$ alkyl, preferably methyl on para position. In another preferred embodiment, $R_2$ is a C$_{1-6}$ alkyl group, preferably methyl.

In above embodiments and hereinafter, where $R_1$ is hydroxyl protecting group (PG), is selected from acetyl, propionyl, benzyl, 2-nitrobenzyl, 4-nitrobenzyl, p-methoxybenzyl, p-methoxybenzylcarbonyl, 2,3-dimethoxybenzyl, 2,4-dimethoxybenzyl, 3,4-dimethoxybenzyl, benzoyl, benzyloxycarbonyl, p-methoxybenzyloxycarbonyl, carboethoxy, carbomethoxy, t-butoxycarbonyl, 2,2,2-trichloroethoxycarbonyl, 2-(trimethylsilyl) ethoxycarbonyl, 2-(4-trifluoromethylphenylsulfonyl)ethoxy carbonyl, tri(C1-4-alkyl)silyl, tert-butyldimethylsilyl, tertbutyldiphenylsilyl, methoxymethyl ether, 2-tetrahydropyranyl, allylether, 9-fluorenylmethyl, 9-fluorenylmethyloxycarbonyl, 1-adamantyloxycarbonyl, 2-adamantyl carbonyl, 2,4-dimethylpent-3-yloxycarbonyl, cyclohexyloxycarbonyl, 1,1-dimethyl-2,2,2-trichloroethoxycarbonyl, vinyl, 2-phenylsulfonyl ethyl, diphenyl-4-pyridylmethyl, N',N'-dimethylhydrazinyl, t-butoxymethyl, benzyloxymethyl, 1-(ethoxy)ethyl, triphenylmethyl, diphenylmethyl, N-pivaloyloxymethyl, 1,1-diethoxymethyl.

Suitable solvent(s) in the above embodiments and hereinafter may be selected from hydrocarbon solvents such as n-hexane, n-heptane, cyclohexane, toluene, pentane, cycloheptane, methylcyclohexane, ethyl benzene or o-, m- or p-xylenes and the like; ether solvents such as 1,2-dimethoxyethane, tetrahydrofuran, 1,4-dioxane, diethyl ether, ethylene glycol dimethyl ether, ethylene glycol diethyl ether, diethylene glycol dimethyl ether, diethylene glycol diethyl ether, triethylene glycol dimethyl ether, t-butyl methyl ether or diisopropyl ether and the like; ester solvents such as ethyl formate, methyl acetate, ethyl acetate, isopropyl acetate, n-butyl acetate, t-butyl acetate, isobutyl acetate and the like; polar aprotic solvents such as N,N-dimethylacetamide (DMA), N,N-dimethylformamide (DMF), dimethylsulfoxide (DMSO), N-methylpyrrolidone (NMP) and the like; chlorinated solvents such as dichloromethane, chloroform and the like; ketone solvents such as acetone, methyl ethyl ketone, 2-pentanone, 3-pentanone, methyl butyl ketone, methyl isobutyl ketone and the like; nitrile solvents such as acetonitrile and the like; alcoholic solvents such as methanol, ethanol, n-propanol, isopropanol, n-butanol, isobutanol, t-butanol, 2-fluoroethanol, 2,2,2-trifluoroethanol, ethylene glycol, 2-methoxyethanol, 2-ethoxyethanol, diethylene glycol, diethylene glycol mono methyl ether, cyclohexanol and the like; polar protic solvents such as water or mixtures thereof.

Examples of a base in the above reaction and hereinafter, include without limitation, inorganic bases selected from alkali metal hydroxides such as lithium hydroxide, sodium hydroxide, potassium hydroxide and the like; alkali metal carbonates such as sodium carbonate, potassium carbonate, lithium carbonate and the like; alkali metal bicarbonates such as sodium bicarbonate, potassium bicarbonate, lithium bicarbonate and the like and ammonia; organic bases selected from alkali metal alkoxides such as sodium methoxide, sodium ethoxide, sodium tertbutoxide, potassium tert-butoxide and the like; triethylamine, methylamine, ethylamine, 1,5-diazabicyclo(4.3.0)non-5-ene (DBN), 1,8-diazabicyclo[5.4.0]undec-7-ene (DBU), 1,4-diazabicyclo[2.2.2]octane (DABCO), diisopropylamine, diisopropylethylamine, N-methylmorpholine, N-ethylmorpholine, piperidine, N,N-dimethylaminopyridine, pyridine, 2,6-lutidine, 2,4,6-collidine, 1-methylimidazole, 1,2,4-triazole or mixtures thereof.

Examples of phase transfer catalysts include without limitation, crown ethers selected from 12-crown-4, 15-crown-5 or 18-crown-6; poly(ethylene glycol) (PEG) and derivatives; and quaternary ammonium compounds selected from tetramethyl ammonium bromide, tetrabutyl ammonium bromide, tetrabutylammonium chloride methyl triethyl ammonium bromide, benzyl trimethyl ammonium bromide, benzyl triethyl ammonium bromide and the like.

In a preferred embodiment of the invention for preparing empagliflozin, the hydroxyl protecting group in compound (7) is acetyl; base is selected from sodium hydroxide, potassium hydroxide, sodium carbonate and potassium carbonate; solvent is selected from acetone, acetonitrile, 1,4-dioxane and toluene; and phase transfer catalyst is selected from 18-crown-6, PEG and tetrabutyl ammonium bromide.

The reaction of compound (7) with compound (8) is carried out at temperature of about 75-115° C.

In a second embodiment, the present invention provides a modified, improved process for preparing (1S)-1,5-anhydro-1-C-[4-chloro-3-[(4-ethoxyphenyl)methyl] phenyl]-D-glucitol i.e., dapagliflozin, solvates or hydrates thereof, comprising reacting a compound (7) in a suitable solvent with compound (8) in the presence of a base and optionally a phase transfer catalyst, as given below:

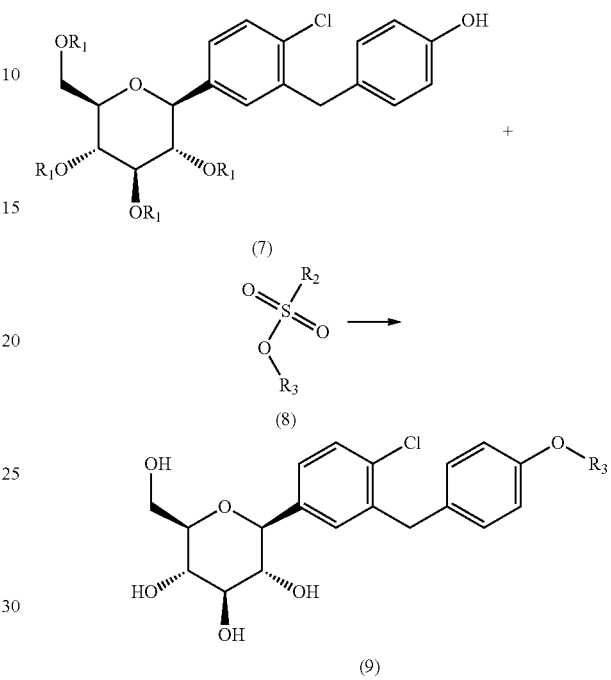

Wherein $R_1$ is hydrogen or a hydroxyl protecting group selected from —C(O)OC$_1$-C$_6$ alkyl, optionally substituted —C(O)OC$_1$-C$_6$ aryl, optionally substituted —C$_1$-C$_{12}$ aryl (C$_1$-C$_3$)alkyl, optionally substituted C$_7$-C$_{11}$ aryl carbonyl, —C(O)C$_1$-C$_6$ alkyl, C$_1$-C$_6$ alkylsulfonyl; $R_2$ is trifluoromethyl, C$_{1-6}$ alkyl, or an aryl group optionally substituted at para position with groups such as halogen, C$_{1-6}$ alkyl; and $R_3$ is ethyl. In one preferred embodiment, $R_2$ is an aryl group, preferably phenyl. In another embodiment, $R_2$ is phenyl substituted with a C$_{1-6}$ alkyl, preferably methyl on para position. In another preferred embodiment, $R_2$ is a C$_{1-6}$ alkyl group, preferably methyl.

In the above process for preparing dapagliflozin, the base, solvent and phase transfer catalyst are defined as hereinbefore.

In an alternative embodiment, where $R_1$ is hydrogen, compound (7) in a suitable solvent is reacted with compound (8) in the presence of a base and optionally a phase transfer catalyst, where $R_2$ and $R_3$ are defined as hereinbefore to form empagliflozin or dapagliflozin respectively.

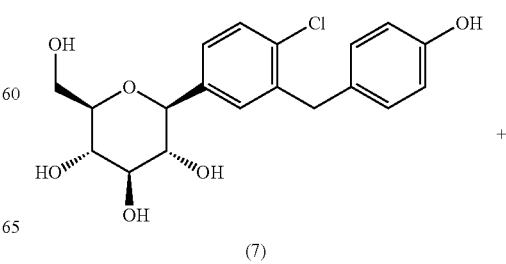

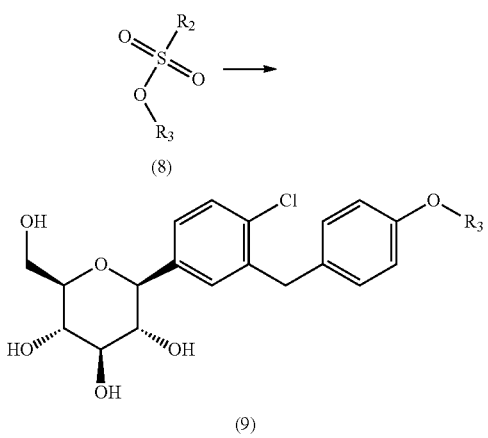

(8)

(9)

In a third embodiment, the present invention provides a cost-effective, integrated process for preparing the compound (7), useful as a common intermediate for preparing empagliflozin as well as dapagliflozin and said process comprises:

(a) reacting a diphenylketone compound (1) with a reducing agent in the presence of a Lewis acid and a solvent to obtain a diphenylmethane compound (2);

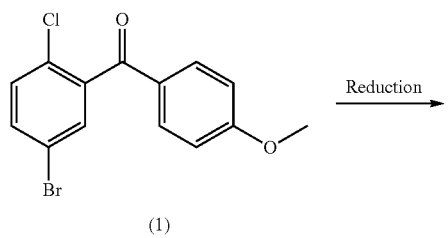

(1)

(2)

(b) coupling the diphenylmethane compound (2) with a protected gluconolactone (3) in a suitable solvent in the presence of an alkyl lithium, followed by treatment with an acid to obtain a compound (4);

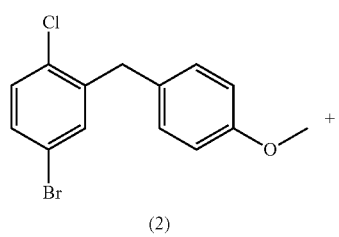

(2)

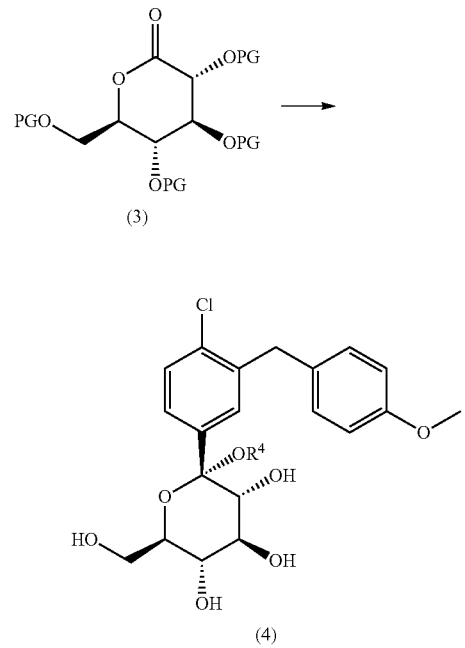

(3)

(4)

wherein in compound (3), PG is a hydroxyl protecting groups selected from the groups described as hereinbefore and $R^4$ in compound (4) represents hydrogen or $C_{1-4}$ alkyl;

(c) treating the compound (4) with a suitable reagent in the presence of a base, wherein the hydroxyl groups are protected to form a compound (5), wherein PG and $R^4$ are as defined hereinbefore;

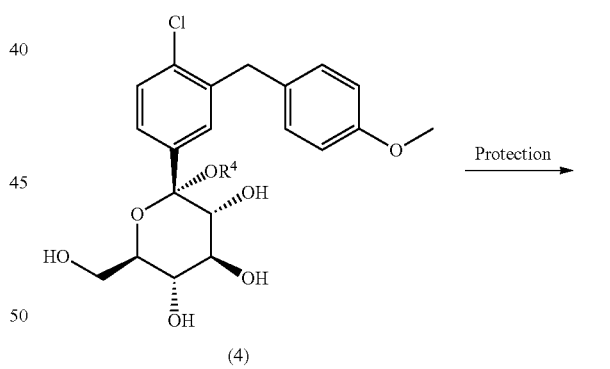

(4)

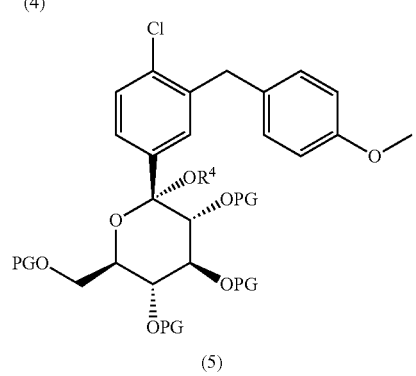

(5)

or subjecting the compound (4) obtained from step (b) to reduction to obtain a compound (5a);

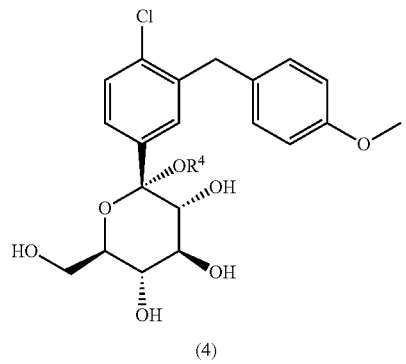

(4)

Reduction →

Or reacting the compound (5a) obtained from step (c) with suitable reagent to protect the hydroxyl groups in the presence of a base to form a compound (6); and

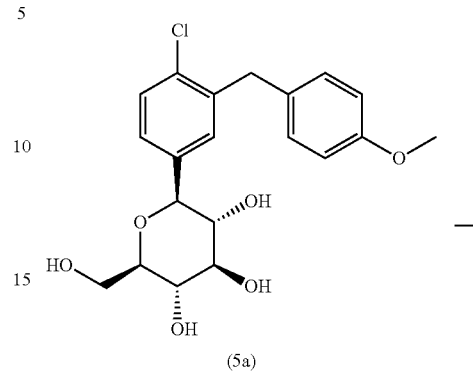

(5a)

(d) reacting the compound (5) from step (c) with a reducing agent in the presence of a Lewis acid and a suitable solvent to form a compound (6);

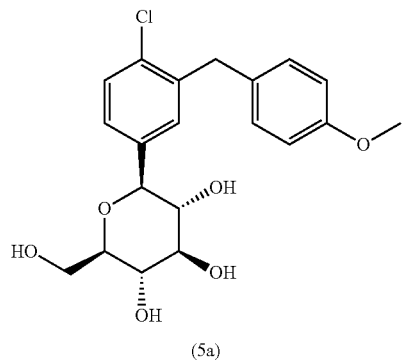

(5a)

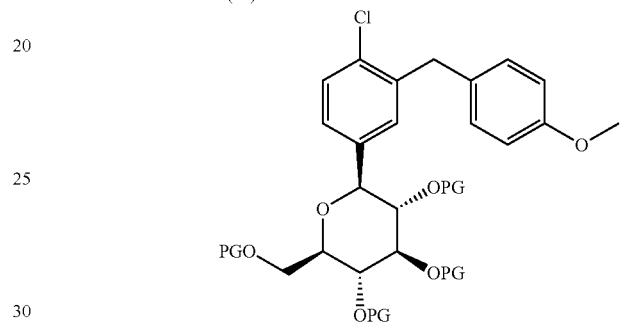

(6)

(e) subjecting the compound (6) to 0-demethylation in a suitable solvent in the presence of a reagent-pair and a suitable reagent, wherein PG and $R_1$ are as defined hereinbefore,

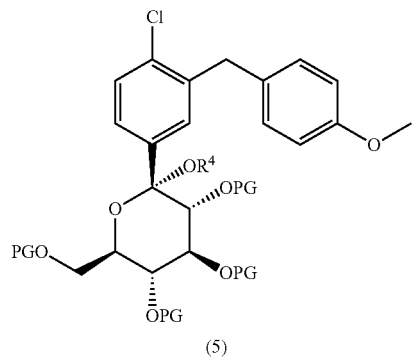

(5)

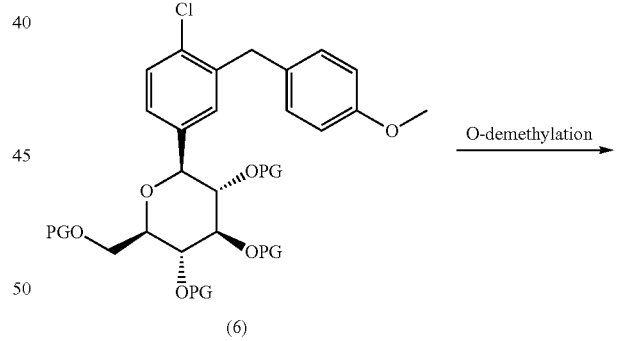

(6)  O-demethylation →

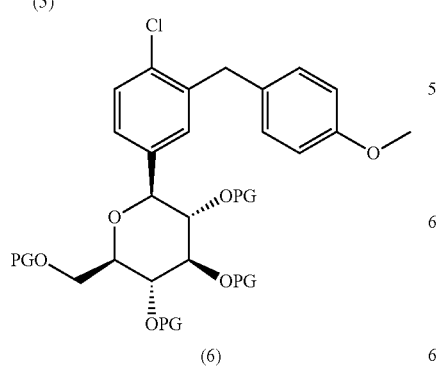

(6)

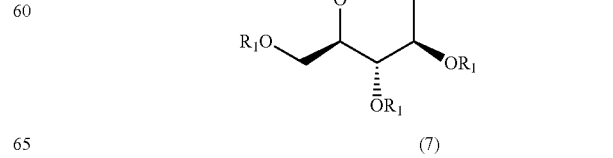

(7)

Wherein in step (a) reduction is carried out using a reducing agent in the presence of or without a Lewis acid or suitable Bronsted acids such as hydrochloric acid, toluenesulfonic acid, trifluoroacetic acid or acetic acid.

Examples of reducing agent include without limitation, silanes such as triethylsilane, tripropylsilane, triisopropylsilane or diphenylsilane: hydrides such as sodium borohydride, sodium cyanoborohydride, zinc borohydride, borane complexes, lithium aluminum hydride, diisobutylaluminum hydride, vitride and the like. Examples of lewis acid include without limitation, aluminum chloride, boron trifluoride etherate, copper (II) triflate, iron (III) chloride, tin (II) chloride, tin tetrachloride, zinc chloride, zinc iodide, indium (III) chloride, scandium triflate, trimethylsilyl triflate, trifluoroacetic acid and the like. Lewis acids may be used in stoichiometric or excess quantities.

The reaction is carried out in a solvent at temperature ranging between 60-75° C. The solvent is preferably selected in view of the reducing agent and the optional Lewis acid. In preferred embodiments, step (a) is performed using sodium borohydride in the presence of aluminum chloride in tetrahydrofuran.

In the present context, compound (1) used in step (a) may be prepared according to the methods known in the art.

In step (b), the alkyl lithium is selected from n-, sec-, and tert-butyl lithium, preferably n-butyl lithium is used. Examples for acid include without limitation, methanesulfonic acid, toluenesulfonic acid, hydrochloric acid, sulphuric acid, acetic acid, ammonium chloride and the like. The reaction is carried out at temperature ranging between −70 to −80° C.

Preferably diphenylmethane compound (2) is reacted with protected gluconolactone (3) (where PG is trimethylsilyl) in tetrahydrofuran in the presence of n-butyl lithium, followed by treatment with concentrated hydrochloric acid to form compound (4), wherein $R^4$ represents hydrogen or $C_{1-4}$ alkyl. In one preferred embodiment, $R^4$ represents hydrogen. In another preferred embodiment, $R^4$ represents methyl group.

The compound (3) may be obtained from commercially available sources or prepared according to methods known in the literature.

In steps (c) and (d), reaction is carried out in the presence of a suitable reagent and a base for introducing the hydroxyl protecting group. In preferred embodiments, compound (4) and compound (5a) is treated with acetic anhydride in the presence of N,N-dimethylaminopyridine (DMAP) and dichloromethane. This step is carried out at a temperature of about 30-40° C.

In steps (c) and (d), the reduction is carried out using a reducing agent mentioned as hereinbefore. In preferred embodiments, reduction is carried out using triethylsilane in the presence of boron trifluoride etherate in dichloromethane. The reduction is carried out at a temperature of about −40 to −60° C.

In step (e), thiourea and aluminium chloride ($AlCl_3$) form together a reagent pair. In thiourea/$AlCl_3$ reagent pair, the sulphur atom acts as a weak nucleophile and is capable of cleaving a methyl group from a methoxy, similar to the $AlCl_3$/Triethylsilane reagent.

Demethylation step may be carried out using a suitable reagent known in the art such as hydrogen bromide, boron tribromide, thiols such as dodecanethiol, decanethiol, cyclohexane thiol, cyclopentane thiol, cyclobutane thiol, thiophenol, methanethiol, ethanethiol, 1-propanethiol, 2-propanethiol, n-butanethiol, propanedithiol, 1,3-butanedithiol, 1,4-butanedithiol in the presence of a suitable solvent to yield a compound (7). The choice of solvent depends on the type of reagent used.

In more preferred embodiments of the invention, O-demethylation is performed using dodecanethiol and thiourea-aluminium chloride reagent pair in dichloromethane resulting in the desired compound (7) with higher purity and better yields compared to dodecanethiol or any other thiol reagent which when used alone.

The reagent pair is found to be advantageous when compared to hydrogen bromide or boron tribromide.

In an embodiment, the modified, improved process of the present invention for preparing compound (7) is as represented in Scheme A:

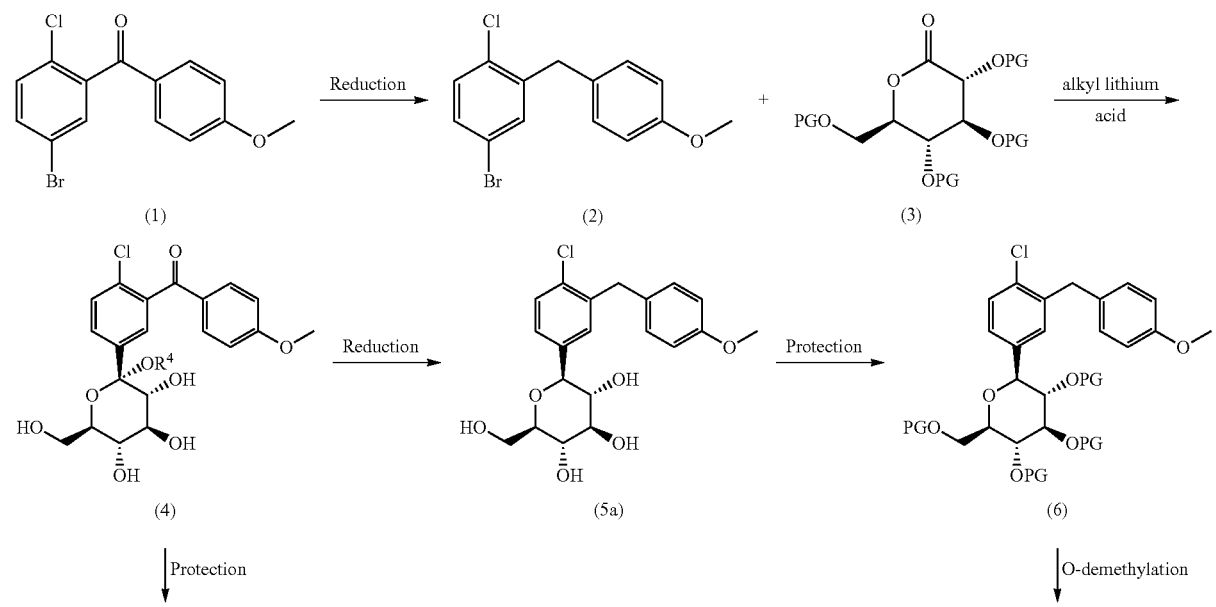

Scheme A

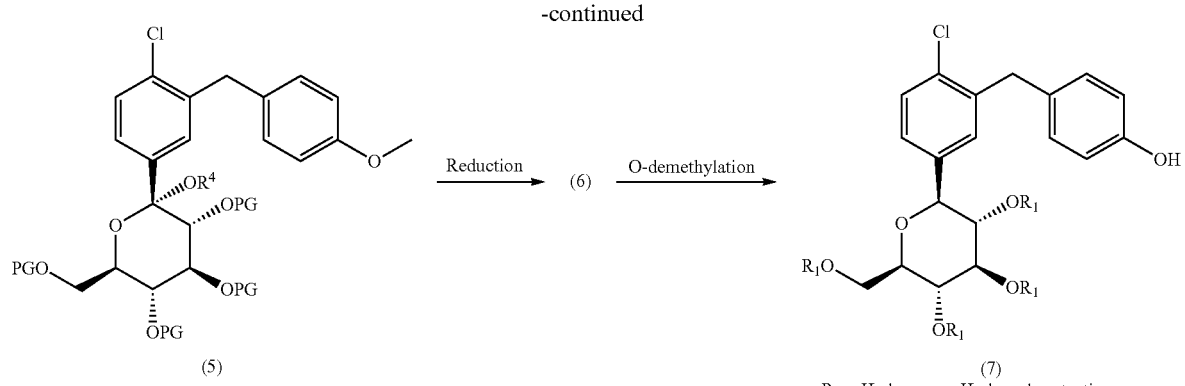

In one preferred embodiment, where PG is an acetyl group, compound (6) is subjected to O-demethylation using thiourea-AlCl$_3$ and dodecanethiol in dichloromethane to form compound (7), wherein R$_1$ is hydroxyl protecting group, preferably an acetyl group.

In another preferred embodiment, where PG is an acetyl group, compound (6) is subjected to hydrolysis to first cleave the hydroxyl protecting groups, followed by cleaving the phenolic methyl ether to yield the compound (7), wherein R$_1$ is hydrogen.

In one embodiment, the process for preparing the compound (7) useful as a common intermediate for preparing empagliflozin as well as dapagliflozin, is described in scheme B.

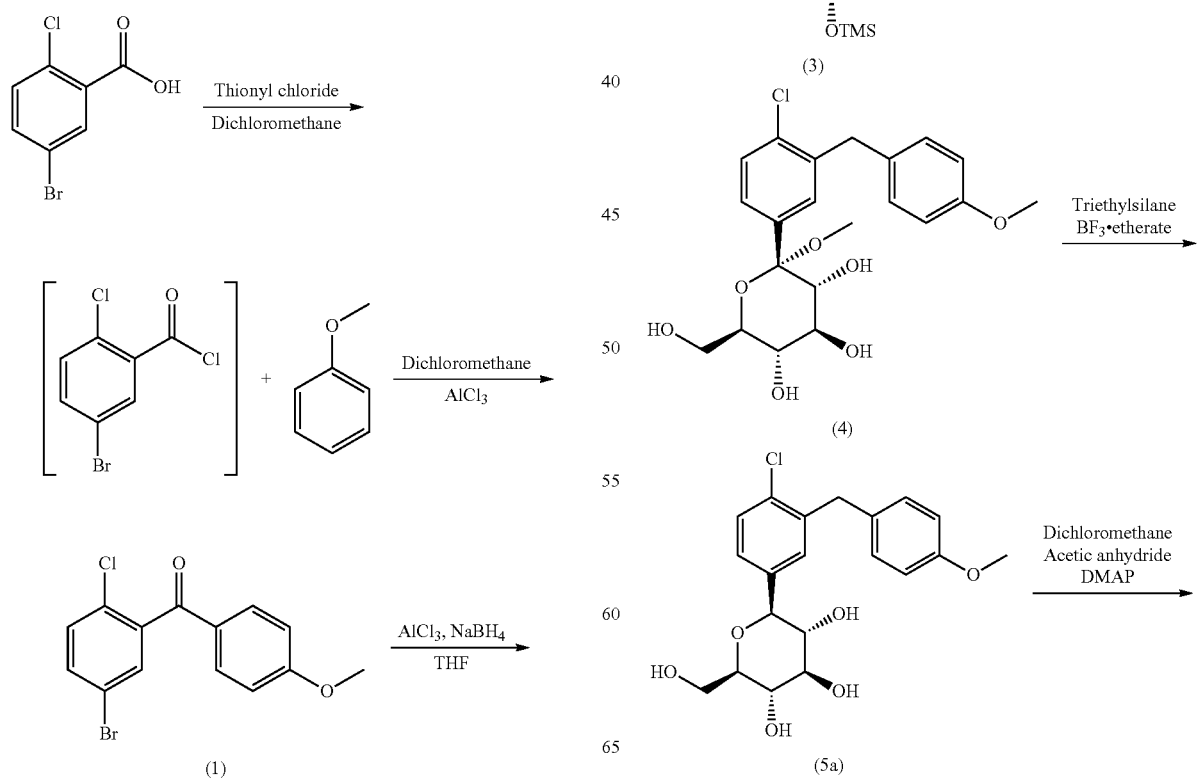

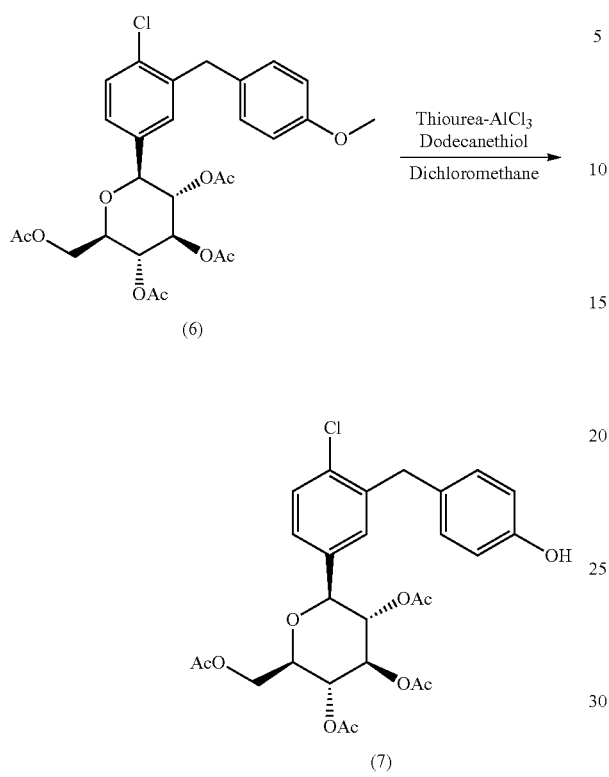
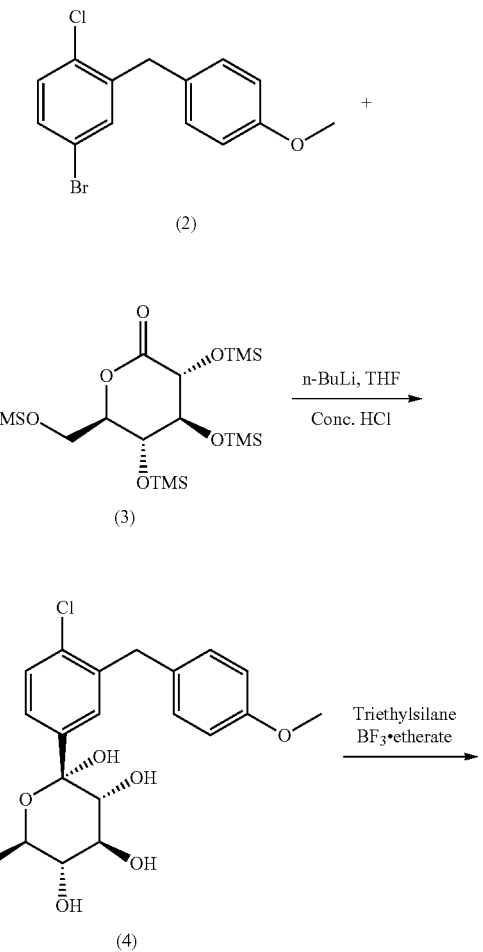
In another embodiment, the process for preparing the compound (7) useful as a common intermediate for preparing empagliflozin as well as dapagliflozin, is described in the following scheme C.
Scheme C
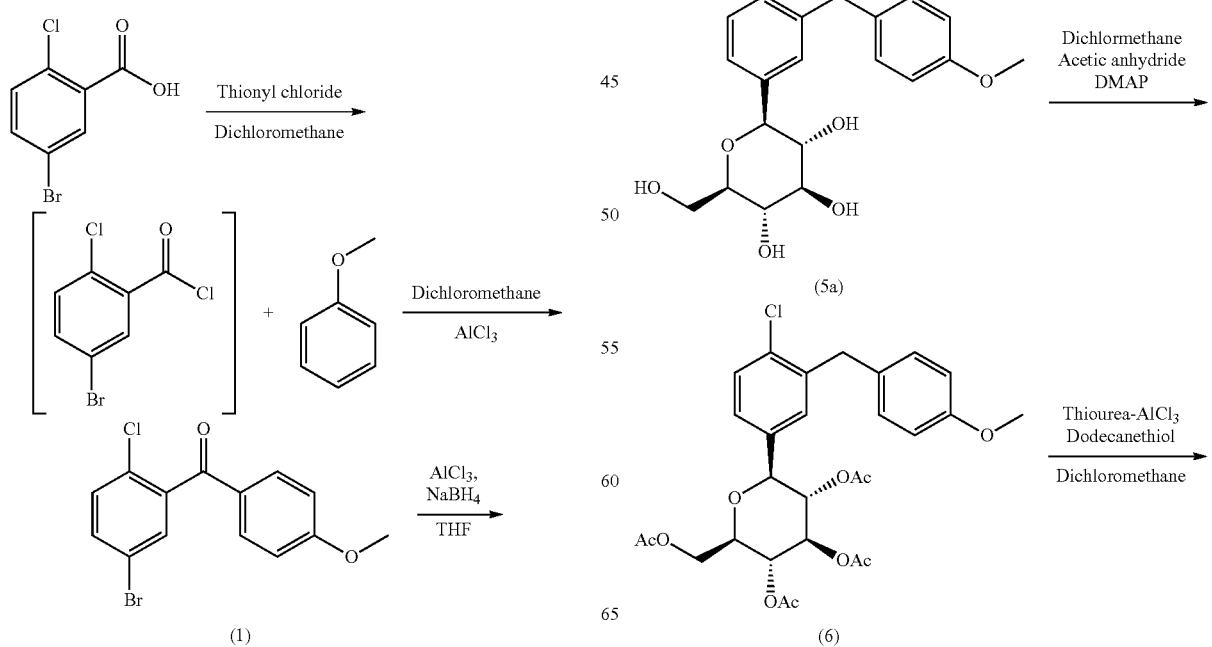

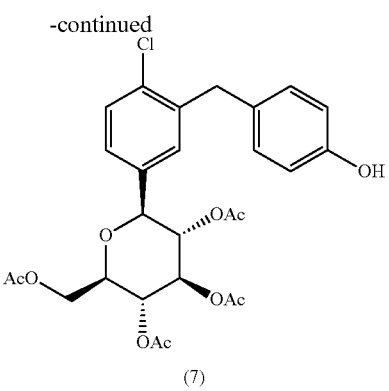

(7)

In a fourth embodiment, the present invention provides a process for preparing compound (8), where $R_2$ is trifluoromethyl, $C_{1-6}$ alkyl, or an aryl group optionally substituted at para position with groups such as halogen, $C_{1-6}$ alkyl and $R_3$ is (R)-tetrahydrofuran-3-yl. The process of the present invention for preparing compound (8) is represented in Scheme D.

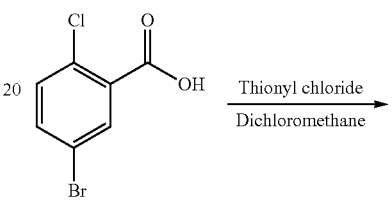

According to Scheme-D, (S)-3-hydroxytetrahydrofuran (i) in a suitable solvent is treated with an alkyl or aryl sulfonyl chloride compound (ii), wherein $R_2$ is selected from $C_{1-6}$ alkyl, trifluoromethyl or an aryl group optionally substituted at para position with groups such as halogen, nitro, $C_{1-6}$ alkyl, in the presence of a base to give a compound (iii), which is reacted with alkali metal acetate such as lithium acetate, sodium acetate, potassium acetate or cesium acetate, optionally in the presence of a phase transfer catalyst to obtain a compound (iv). Suitable phase transfer catalysts (PTC) include crown ethers such as 12-crown-4, 15-crown-5 or 18-crown-6. In preferred embodiments alkali metal acetate used is potassium acetate and the phase transfer catalyst is 18-crown-6.

Further, the compound (iv) is subjected to hydrolysis in the presence of a base to yield (R)-3-hydroxytetrahydrofuran (v), which is further treated with compound (ii) wherein $R_2$ is selected from $C_{1-6}$ alkyl, trifluoromethyl or an aryl group optionally substituted at para position with groups such as halogen, $C_{1-6}$ alkyl to obtain the compound (8) in desired configuration. The compound (8) is further reacted with compound (7) as described hereinbefore to yield empagliflozin in high yields and purity.

In one preferred embodiment, the modified, improved process of the present invention for preparing empagliflozin (9a) is as represented in Scheme E.

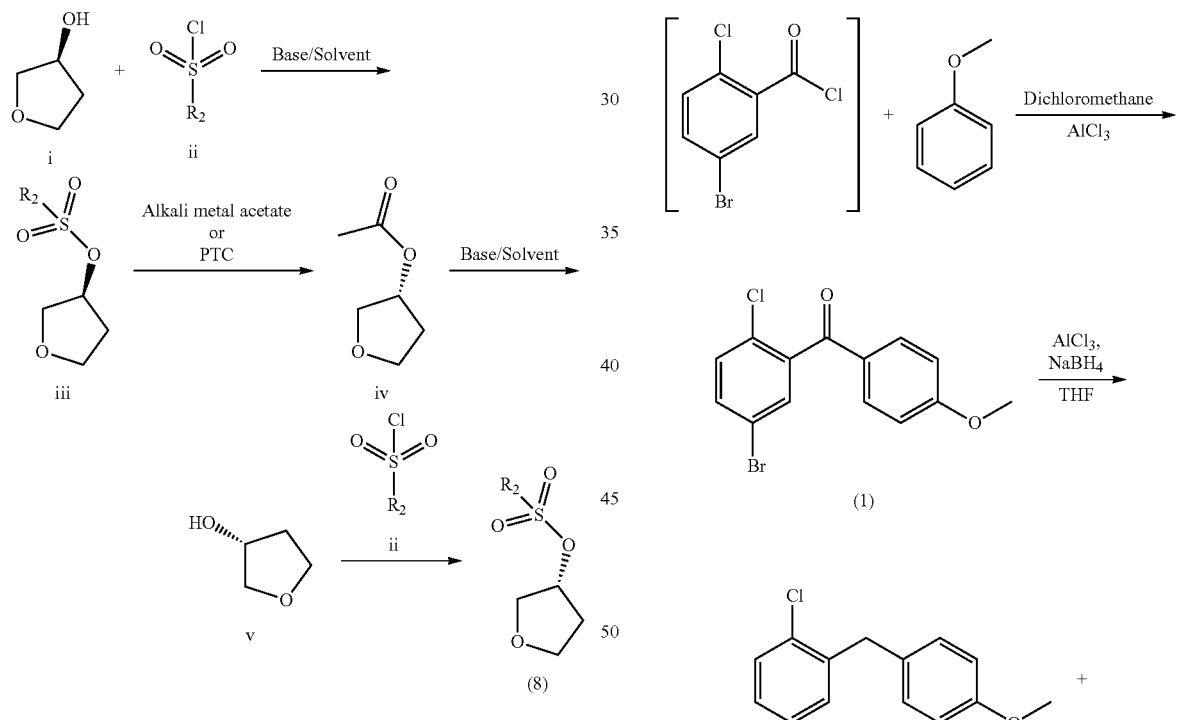

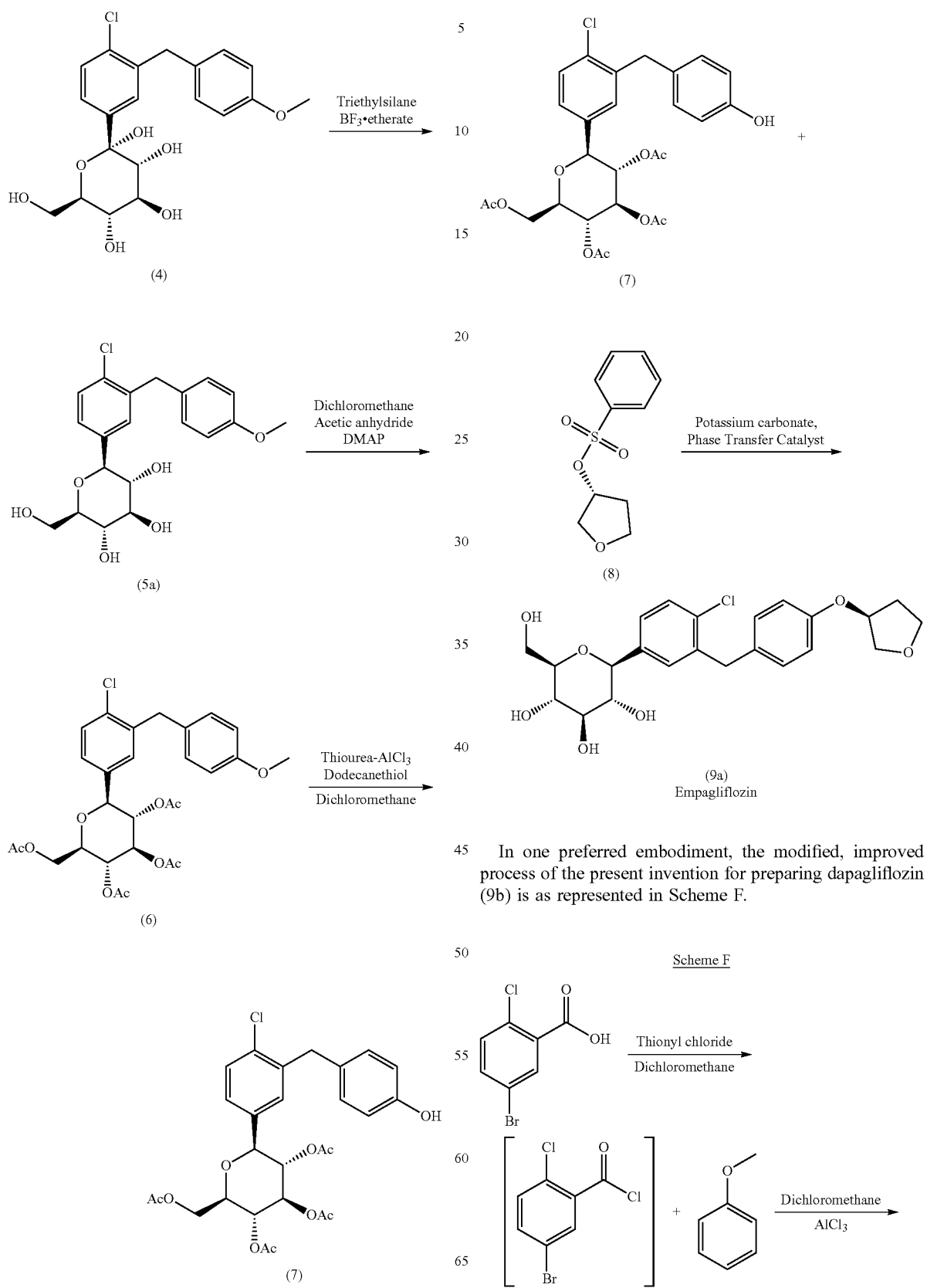
In one preferred embodiment, the modified, improved process of the present invention for preparing dapagliflozin (9b) is as represented in Scheme F.

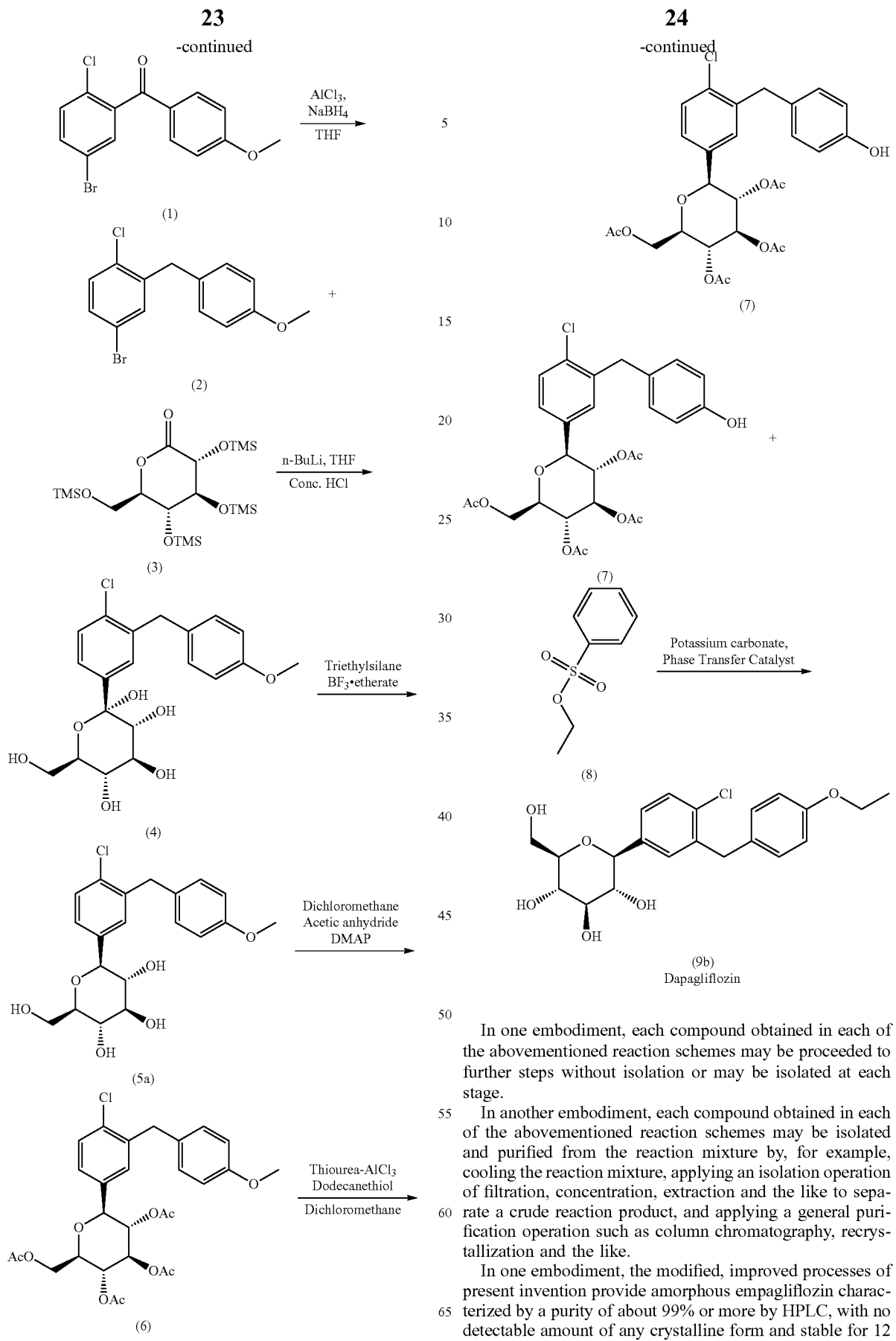

In one embodiment, each compound obtained in each of the abovementioned reaction schemes may be proceeded to further steps without isolation or may be isolated at each stage.

In another embodiment, each compound obtained in each of the abovementioned reaction schemes may be isolated and purified from the reaction mixture by, for example, cooling the reaction mixture, applying an isolation operation of filtration, concentration, extraction and the like to separate a crude reaction product, and applying a general purification operation such as column chromatography, recrystallization and the like.

In one embodiment, the modified, improved processes of present invention provide amorphous empagliflozin characterized by a purity of about 99% or more by HPLC, with no detectable amount of any crystalline form and stable for 12 months on storage at 5±3° C. Preferably, the present invention provides amorphous empagliflozin characterized by a purity of about 99.5% or more by HPLC.

In another embodiment, the present invention provides a process for the preparation of amorphous empagliflozin comprising: a) dissolving crude empagliflozin in a suitable solvent or mixtures thereof; b) optionally filtering the undissolved particles; c) removing the solvent by a suitable technique; and/or d) drying the solid at suitable temperature. The solvent(s) may be selected from any of the solvents described as hereinbefore. Preferably, the solvents are selected from acetonitrile, dichloromethane, methanol, and water.

In another embodiment, the modified, improved processes of present invention provide crystalline empagliflozin characterized by a purity of 99% or more by HPLC, stable for 6 months when stored at a temperature of 40±2° C. and 75±5% relative humidity (RH).

In yet another embodiment, the modified, improved processes of present invention provide crystalline empagliflozin characterized by a purity of 99% or more by HPLC, stable for 6 months when stored at a temperature of 25±2° C. and 60±5% relative humidity (RH).

Further, the present invention provides a process for preparing crystalline empagliflozin, comprising: a) dissolving empagliflozin in a solvent or a mixture of solvents; b) heating and stirring the reaction mixture to a temperature up to 60±5° C. to form a clear solution; c) cooling the reaction mixture to 0-5° C.; d) filtering the solution, followed by drying under vacuum to provide crystalline empagliflozin. The solvent(s) may be selected from any of the solvents described as hereinbefore. Preferably, the solvents are selected from acetonitrile, methanol, water, and dichloromethane.

In yet another embodiment, the present invention provides a process for preparing crystalline dapagliflozin propane-1,2-diol hydrate, wherein the process comprises: a) dissolving crude Dapagliflozin obtained from the modified process of present invention in one or more solvents; b) cooling the reaction mass to a suitable temperature; c) adding propane-1,2-diol to the above reaction mixture at same temperature; d) stirring, filtering and removing the solvent followed by drying to isolate crystalline dapagliflozin propane-1,2-diol. The solvent(s) may be selected from any of the solvents described as hereinbefore.

Suitable techniques that may be used for the removal of solvent include but are not limited to rotational distillation using a device such as rotary evaporator, spray drying, filtration, agitated thin film drying (ATFD), freeze drying (lyophilization) and the like, optionally under reduced pressure.

The resulting solid may be collected by using techniques such as by scraping, or by shaking the container, or other techniques specific to the equipment used.

Drying may be suitably carried out using an air tray dryer, vacuum tray dryer, fluidized bed dryer, spin flash dryer, flash dryer, and the like. The drying may be carried out at atmospheric pressure or under reduced pressures, specifically at temperatures less than about 80° C. and more specifically less than about 60° C. The drying may be carried out for any time period required for obtaining a desired product quality, such as from about 30 minutes to about 24 hours, or longer. The dried product may optionally be subjected to a particle size reduction procedure to produce desired particle sizes and distributions. Milling or micronization may be performed after the completion of drying of the product. Equipment that may be used for particle size reduction includes but not limited to ball mill, roller mill, hammer mill, and jet mill.

In one embodiment, the products obtained from the processes of the present invention may be used for preparation of pharmaceutical formulations useful for the prevention and/or treatment of diseases and conditions associated with SGLT-2 inhibition.

Methods

1. High Performance Liquid Chromatography (HPLC)

(a) (1S)-1,5-anhydro-1-C-[4-chloro-3-[[4-[[(3S)-tetrahydro-3-furanyl]oxy]phenyl] methyl]phenyl]-D-glucitol, i.e., empagliflozin (crystalline)

Apparatus: A liquid chromatographic system is to be equipped with variable wavelength UV-Detector and Integrator.
Column: Promosil C18, 250×4.6 mm, 100 Å, 5 μm or equivalent
Column Temperature: 35° C.
Wavelength: 220 nm
Flow rate: 1.2 mL/min
Injection volume: 5μμL
Run Time: 60 min
Elution: Gradient
Diluent: Acetonitrile: Water (50: 50 v/v)
Mobile phase A: Buffer solution
Mobile phase B: Acetonitrile: Water (90: 10 v/v)
Buffer solution: Transfer accurately about 1 mL of ortho phosphoric acid into 1000 mL of milli-Q water, filter through 0.45 μm nylon membrane and sonicate to degas.

(b) (1S)-1,5-anhydro-1-C-[4-chloro-3-[(4-ethoxyphenyl)methyl] phenyl]-D-glucitol i.e., dapagliflozin propane-1,2-diol monohydrate Chromatographic conditions are same as given under (a), except for:
Wavelength: 225 nm
Run Time: 55 min 2. Powder X-ray Diffraction (PXRD)

The diffraction patterns were measured using Bruker axs and D8 ADVANCE diffractometer equipped with LYNX-EYE XE T detector, used radiation Cu Kα (Å=1.5418 Å), excitation voltage: 40 kV, anode current: 35 mA, measured range; 2-50° 2θ, increment: 0.02° 2θ.

TABLE No. 1

Chemical Purity of Empagliflozin

| Stability Period | Purity by HPLC | | PXRD |
|---|---|---|---|
| | 40 ± 2° C. & 75 ± 5% RH | 25 ± 2° C. & 60 ± 5% RH | |
| Initial | 99.88% | 99.88% | Crystalline |
| 1 month | 99.88% | 99.89% | Crystalline |
| 3 months | 99.87% | 99.87% | Crystalline |
| 6 months | 99.89% | 99.87% | Crystalline |

Advantages of Present Invention

1. The present inventors have surprisingly found that use of a phase transfer catalyst (PTC) in the reaction of compound (7) with compound (8) to obtain compound (9) resulted in an enormous reduction of the reaction time which is highly advantageous at commercial scale involving reduced power consumption and saving time.

Prior art processes does not disclose in any way the use of a phase transfer catalyst in the reaction of compound (7) with compound (8) for the preparation of empagliflozin or dapagliflozin. Table 2 represents the reaction time in prior art processes in comparison with the improved, processes of present invention as given below:

TABLE No. 3

Comparison of Prior Art Process and Present Invention

| | | Prior art | Present invention | Observation |
|---|---|---|---|---|
| Compound (1) | Reagent | Oxalyl chloride | Thionyl Chloride | Thionyl chloride is cheaper and safer chlorinating reagent than oxalyl chloride which is otherwise highly toxic |
| | Yield | 64% | 81% | |
| Compound (2) | Reagent | $Et_3SiH/BF_3 \cdot Et_2O$ (or) $TiCl_4$ | $AlCl_3/NaBH_4$ | Triethylsilane and boron trifluoride etherate are expensive and required in much larger quantities and titanium tetrachloride reacts explosively with water to release HCl. |
| | Yield | 61% | 75% | |
| Compound (7) | Reagent | $BBr_3$ HBr in acetic acid | Dodecanethiol, $AlCl_3$, Thiourea | $BBr_3$ is expensive; with HBr, reaction doesn't complete. |
| | Yield | 65% | 92% | |
| | Purity | 80% | 98.65% | |
| Reaction of compound (7) with (8) | Phase transfer catalyst (PTC) | Not used (Reaction time 48-52 hrs) | 18-crown-6 | Reaction time reduced to 5 hrs |
| | | | TBAB | Reaction time reduced to 24 hrs |
| | | | PEG | Reaction time reduced to 18 hrs |

TABLE No. 2

| Reaction parameter | Reaction Time |
|---|---|
| Absence of PTC | 48-52 hrs |
| TBAB | 24 hrs |
| 18-Crown-6 | 5 hrs |
| Poly(ethylene glycol) | 18 hrs |

2. Use of anisole in the preparation of compound (1), which is further used for preparing empagliflozin and dapagliflozin reduces cost and provides better yields and purities when compared with the use of fluorobenzene (for empagliflozin) and phenetole (for dapagliflozin) as observed in the prior art.

3. Use of Lewis acid such as $TiCl_4$ in the conversion of compound (1) to compound (2) is known in the art. Titanium tetrachloride ($TiCl_4$) is a strong Lewis acid, exothermically forming adducts with even weak bases such as THF and explosively with water and releasing HCl. However, the present invention uses aluminium chloride which is better, cheaper and safer Lewis acid when compared to titanium tetrachloride as used in the prior art.

4. O-demethylation using dodecanethiol and thiourea-aluminium chloride reagent pair provides the desired compound with higher purity and better yields compared to dodecanethiol or any other thiol reagent when used alone. The reagent pair method is advantageous when compared to boron tribromide as well as HBr.

5. Present invention provides a common intermediate (7) for both empagliflozin and dapagliflozin synthesis which is cost effective and the synthesis of the said products becomes highly convergent as opposed to the linear synthetic schemes employed in the prior art.

6. Present inventions provides a simplified, cheaper process for preparation of R-3-hydroxytetrahydrofuran, which is otherwise expensive from a less expensive, commercially available (S)-3-hydroxy tetrahydrofuran.

Further the novel processes for preparing the SGLT-2 inhibitors and novel intermediates thereof, according to the present invention are illustrated in the following examples. The following specific and non-limiting examples are to be construed as merely illustrative, and do not limit the present disclosure in any way whatsoever.

EXAMPLES

Example 1: Preparation of (5-bromo-2-chlorophenyl)(4-methoxyphenyl) Methanone (1)

A solution of 5-bromo-2-chloro benzoic acid (150 g) in dichloromethane (750 mL) was stirred for 15-30 min. Dimethylformamide (0.6 ml) and thionyl chloride (138.7 mL) was charged to the above reaction mass (RM), stirred for 10-15 min. The RM was heated to 40-45° C. and maintained for 2h. After completion of reaction, distilled the RM completely under vacuum at 45° C. Charged dichloromethane (1200 mL) in to the mass, cooled to 0-5° C. Charged aluminum chloride (101.9 g) into the RBF, slowly added anisole (74.2 g) into the mass at same temperature. After the reaction is complete, water (750 mL) was added to the RM, and slightly warmed to 20-30° C. The organic and aqueous layers were separated, the aqueous layer was extracted with dichloromethane (2×750 mL). Then the organic layer was washed with 2N hydrochloric acid solution, dichloromethane (2×750 mL), followed by washing with sodium bicarbonate (2×750 mL). The organic layer was then washed with sodium chloride solution (750 mL) and dried over sodium sulfate. Then distilled the organic layer completely under vacuum at 40° C. to remove the solvent completely. The solid obtained was washed with methanol (300 mL), cooled to 0-5° C. and stirred for 60 min to obtain a precipitate. Filtered the mass and the compound was washed with 100 mL of chilled (about 1° C.) methanol. Then air dried the compound for 6h to obtain the title compound (168.5 g, 81.24%). (Purity by HPLC: 99.22%).

Example 2: Preparation of 2-(4-methoxybenzyl)-4-bromo-1-chlorobenzene (2)

A solution of compound 1 (50 g) from Example 1 and tetrahydrofuran (100 mL) was stirred for 10 min. Cooled the RM to 0-5° C. Aluminum chloride (42.9 g) was charged to the RM at the same temperature, stirred for 30 min at 0-5° C. Sodium borohydride (18 g) was added to the RM, stirred for 60 min at 5-10° C. RM was heated to 65-70° C. and maintained for 15h. After completion of reaction, the RM was cooled to 20-30° C. and then to 0-5° C. Slowly added water (500.0 mL) in to the mass at 5-10° C. Charged ethyl acetate (500 mL) to the RM and stirred for 10 min at 20-30° C. The aqueous and organic layers were separated, aq. layer was extracted with ethyl acetate (250 mL). Organic layer was washed with saturated sodium bicarbonate solution (2×250 mL). Combined organic layers were dried over sodium sulfate. The organic layer was distilled completely under vacuum at 40° C. and residue was treated with methanol (100 mL). Stirred and, cooled the mass to −5 to 0° C. and maintained for 60 min. Filtered the mass and compound was washed with 30 mL of chilled (about 10° C.) methanol. The compound was air dried for 6h to obtain the title compound (36.2 g, 75.65%). (Purity by HPLC: 99.63%).

Example 3: Preparation of (2S, 3R, 4S, 5S, 6R)-2-(4-chloro-3-(4-methoxybenzyl) phenyl)-6-(hydroxymethyl)tetrahydro-2H-pyran-2,3,4,5-tetraol (4)

A mixture of toluene (300 mL) and 50 g of compound (2) from example 4 was heated to 110-115° C. and stirred for 90 min. Charged 113 g of protected lactone (3) (wherein PG=trimethylsilyl) and tetrahydrofuran (350 mL) in to the RM. Cooled the RM to −70 to −75° C. and slowly added n-butyl lithium (216 mL) to the RM at same temperature and maintained for 1.5-2 hrs. After completion of reaction, slowly added hydrochloric acid solution. Then the mass was warmed to 20-30° C. and maintained for 3h. The pH of the RM was adjusted to 8.0 by using saturated sodium bicarbonate solution. Aqueous and organic layers were separated. The organic layer was distilled completely under vacuum at 50° C. After removal of solvent, ethyl acetate was added and stirred for 10 min. Aq and organic layers were separated and combined organic layers were washed with sat. Sodium chloride solution (200 mL). Organic layer dried with sodium sulfate and distilled the organic layer under vacuum at 50° C. to obtain a wet residue containing the title compound (4).

Example 4: Preparation of Compound (5) (PG=Acetyl)

To the residue obtained from Example 3, was added dichloromethane (400 mL), followed by addition of N,N-dimethylaminopyridine (3.5 g) and acetic anhydride (82.3 g).The RM was stirred for 12h at 20-30° C. After the completion of reaction, water (250 ml) was added to the RM and stirred for 10 min. Aqueous and organic layers were separated. The aqueous layer was extracted with dichloromethane (100 mL). Total organic layer were combined and 250 ml of 2N hydrochloric acid solution was added. Stirred the RM for 5 min. Layers were separated, followed by washing with water (250 mL) and stirred for 10 min. Combined organic layers were dried with 20 g of sodium sulfate. The organic layer was distilled completely under vacuum at 45° C. After distillation methanol (100 mL) was charged and distilled completely under vacuum, to obtain a residue containing the compound (5).

Example 5: Preparation of Compound (6)

To the residue obtained from Example 4 was added dichloromethane (250 mL) and acetonitrile (250 mL) in to the RB flask. The reaction mass was cooled to −60±5° C. and slowly added triethylsilane (35.5 g) at the same temperature and stirred for 5 min. Borontrifluoride etherate (52 g) was slowly added to the reaction mass at −60±5° C. Warmed the mass to 20-30° C. After completion of reaction, charged ethyl acetate (500 mL) in to the RM and stirred for 5 min. Aqueous and organic layers were separated and extracted with ethyl acetate (500 mL). Combined the total organic layers and dried over anhydrous sodium sulfate. Distilled the organic layer completely under vacuum at 55° C. followed by washing with methanol and removing the solvent to yield the compound (6) (36 g). (Purity by HPLC: 99.16%)

Example 6: Preparation of Compound (5a)

The compound 5a was prepared from compound 4 using the conditions and reagents as described under Example 5.

Example 7: Preparation of Compound (6) from Compound 5a

Compound 6 was prepared from compound 5a using the conditions and reagents described under Example 4.

Example 8: Preparation of Compound (7)

To compound 6 (2 g) obtained from example 5 or example 7, was added dichloromethane (15 mL), and cooled the mass to −5 to −10° C. Slowly added 20 mL of dodecanethiol & thiourea-AlCl3 to the reaction mass. After completion of reaction, water (50 mL) and dichloromethane (20 mL) was added at 0-5° C. Stirred and aqueous and organic layers were separated. The aqueous layer was extracted with dichloromethane. Combined organic layers were dried with anhydrous sodium sulfate after washing with water. The organic layer was distilled completely under vacuum at 40° C. and dried for 4h to yield the title compound (1.8 g, 92.31%) (Purity by HPLC: 98.65%).

Example 9: Preparation of compound (8) ($R_2$=phenyl; $R_3$=ethyl)

To a solution of ethanol (15.64 g, 0.34 mol) and triethylamine (0.4 mol) in THF (75 mL) at 10° C., was added alkyl or aryl sulfonyl chloride (0.4 mol) in three portions. The RM was stirred for 3h at RT and diluted with hexanes (50 mL). The precipitated triethylamine hydrochloride was filtered and the filtrate was evaporated under vacuum to obtain compound (8) as a syrup which was taken to next step without further purification.

Example 10: Preparation of Compound (8) ($R_3$=(R)-tetrahydrofuran-3-yl)

(a) Preparation of Compound III:

To a solution of (S)-3-hydroxytetrahydrofuran (30 g, 0.34 mol) and triethylamine (0.4 mol) in THF (150 mL) at 10° C., was added alkyl or aryl sulfonyl chloride (0.4 mol) in three portions. The RM was stirred for 3h at RT and diluted with hexanes (75 mL). The precipitated triethylamine hydrochloride was filtered and the filtrate was evaporated under vacuum to obtain the corresponding sulfonate as a syrup which was taken to next step without further purification.

(b) Preparation of Compound iv:

Toluene (200 mL) was added to the residue obtained from step (a) followed by potassium acetate (0.4 mol) and 18-crown-6 (0.04 mol) and the RM was refluxed for 20 h. The RM was cooled to RT, water (100 mL) was added and stirred at RT for 30 min. The organic layer was separated, dried over anhydrous sodium sulfate and the solvent was distilled completely under vacuum to obtain (R)-3-acetoxytetrahydrofuran (iv) as an oil. This reaction can also be performed in the absence of 18-crown-6 without affecting yield and purity of the product.

(c) Preparation of Compound v:

The oil obtained from step (b) was dissolved in methanol (150 mL) containing sodium hydroxide (0.4 mol) at RT. The RM was stirred at RT for 4 h. The solvent was removed under vacuum and the residue was diluted with dichloromethane (150 mL). The organic layer was washed with water (2×100 mL) and the organic layer was dried over anhydrous sodium sulfate and the solvent was removed under vacuum to obtain (R)-3-hydroxy tetrahydrofuran as an oil which was purified by vacuum distillation (24 g, 80% overall)

(c) Preparation of Compound (8):

To a solution of (R)-3-hydroxytetrahydrofuran (20 g, 0.23 mol) from step (c) and triethylamine (0.27 mol) in THF (125 mL) at 10° C., was added alkyl or aryl sulfonyl chloride (0.27 mol) in three portions. The RM was stirred for 3h at RT and diluted with hexanes (65 mL). The precipitated triethylamine hydrochloride was filtered and the filtrate was evaporated under vacuum to obtain compound (8) as a syrup which was taken to next step without further purification.

Example 11: Preparation of (R)-tetrahydrofuran-3-yl benzenesulfonate (8)

To a solution of (R)-3-Hydroxy tetrahydrofuran (50 g) in toluene (260 mL), was charged N,N-Dimethyl amino pyridine (5 g), triethylamine (120 g) and stirred for 5-10 min. the RM was cooled to 0±5° C. Slowly benzene sulfonyl chloride (135 g) was added to the RM at same temperature and slightly warmed to 25±5° C., maintained for 14-15 hrs. After completion of reaction, hydrochloric acid solution was added to the RM at 0-15° C. and stirred for 10-15 min. Layer separation performed and aq. layer extracted with dichloromethane (105 mL), stirred for 10-15 min. Extraction with dichloromethane was repeated once again. To the total organic layer, was charged water (105 mL), stirred and treated with sodium bicarbonate solution. Aqueous and organic layers were separated and the organic layer was distilled completely under vacuum at below 50° C. to give a wet compound (8)

Example 12: Preparation of Amorphous Empagliflozin (9a)

To Compound (7) (25 g), obtained from example 8, was charged acetonitrile (250 mL) in to the RB flask, followed by addition of potassium carbonate (25 g). The RM was stirred for 10 min at 20-30° C. Compound (8) (15 g), obtained from example 10, was charged to the RM, heated to 70-75° C. and stirred for 36h. After completion of the reaction, the RM was cooled to 10-15° C. Slowly water (250 mL) was added followed by addition of ethyl acetate (250 mL), stirred for 10 min. The aqueous and organic layers were separated. The organic layer was dried over anhydrous sodium sulfate and the solvent was distilled under vacuum to obtain the crude product which was chromatographed on silica gel (60-120 mesh) beginning 5% methanol in dichloromethane and gradually increased the polarity to 50% methanol in dichloromethane. The product fractions were distilled off under vacuum at 45° C. to obtain empagliflozin in amorphous form. (15 g). (Purity by HPLC: 99.88%) (PXRD pattern: Amorphous)

Example 13: Preparation of Crystalline Empagliflozin (9a)

To a solution of compound 7 (150 g) from Example 8 in acetonitrile (3 L), was charged compound 8 obtained from Example 11, stirred for 15-20 mins at RT. Potassium carbonate (150 g) was charged to the above RM, the RM was heated to 80±5° C. and stirred for about 50 hrs. After completion of reaction, the RM was cooled to 60±5° C., followed by addition of methanol and stirred for 30-45 min. the RM was cooled to 45±5° C. The solid obtained was filtered and the filtrate was distilled completely under vacuum at below 50° C. The resultant mass was cooled to 20-30° C. and extracted with water (750 mL) and ethyl acetate (600 mL) and stirred for 10-15 min. Aq and organic layers were separated. The organic layer was cooled to 0±5° C. and stirred for 60 min. The resulting solid was filtered and suck dried to give empagliflozin. To the wet compound, was added methanol (180 mL), acetonitrile (180 mL) and water (360 mL). The RM was heated to 60±5° C. and stirred for 30 min until a clear solution was obtained. The RM was cooled to 0±5° C., filtered, followed by drying to yield crystalline empagliflozin (HPLC purity: 99.88%)

Example 14: Preparation of Empagliflozin Using Phase Transfer Catalyst

Using 18-Crown-6: To a solution of compound 7 (150 g) from Example 8 in toluene (1.5 L), was charged compound 8 (65 g) obtained from Example 11, stirred for 15-20 mins at RT. Potassium carbonate (150 g), 18-crown-6 (6 g) was charged to the above RM, the RM was heated to 110±5° C. and stirred for 5±1 hrs. After completion of reaction, the RM was cooled to 60±5° C. Toluene was distilled completely under vacuum at this temperature. The RM was cooled to 30±5° C., charged with methanol (750 mL), water (150 mL) and sodium carbonate (75 g), stirred for 10-15 min. The aqueous and organic layers were separated. Aq. layer was extracted with ethyl acetate (300 mL) and stirred for 10-15 mins. The organic layer was charged with water (750 mL) and stirred for 10-15 min. The total organic layer was cooled to 0±5° C. and stirred for 60-70 min at same temperature. The obtained solid was filtered and washed with ethyl acetate (75 mL). The wet compound was suck dried for 45-60 min at 50° C. to yield crystalline empagliflozin (HPLC purity: 99.95%)

Using poly(ethylene glycol): To a solution of compound 7 (150 g) from Example 8 in toluene (1.5 L), was charged compound 8 (65 g) obtained from Example 11, stirred for 15-20 mins at RT. Potassium carbonate (150 g), PEG (25 g) was charged to the above RM, the RM was heated to 110±5° C. and stirred for 18±1 hrs. After completion of reaction, the RM was cooled to 60±5° C. Toluene was distilled completely under vacuum at this temperature. The RM was cooled to 30±5° C., charged with methanol (750 mL), water (150 mL) and sodium carbonate (75 g), stirred for 3-4 hrs at 30±5° C. The solid was filtered and washed with methanol (300 mL). The filtrate was distilled completely under vacuum at below 50° C. The RM was cooled to 20-30° C., charged with water (750 mL) and ethyl acetate (750 mL), stirred for 10-15 min. The aqueous and organic layers were separated. Aq. layer was extracted with ethyl acetate (300 mL) and stirred for 10-15 mins. The organic layer was charged with water (750 mL) and stirred for 10-15 mins. The total organic layer was cooled to 0±5° C. and stirred for 60-70 min at same temperature. The obtained solid was filtered and washed with ethyl acetate (75 mL). The wet compound was suck dried for 45-60 min at 50° C. to yield crystalline empagliflozin (HPLC purity: 99.92%)

Using Tetrabutylammoniumbromide (TBAB): To a solution of compound 7 (150 g) from Example 8 in acetone (1.5 L), was charged compound 8 (65 g) obtained from Example 11, stirred for 15-20 mins at RT. Potassium carbonate (150 g), TBAB (25 g) was charged to the above RM, the RM was heated to 60±5° C. and stirred for 24±1 hrs. After completion of reaction, the RM was cooled to 60±5° C. Acetone was distilled completely under vacuum at this temperature. The RM was cooled to 30±5° C., charged with methanol (750 mL), water (150 mL) and sodium carbonate 75 g), stirred for 3-4 hrs at 30±5° C. The solid was filtered and washed with methanol (300 mL). The filtrate was distilled completely under vacuum at below 50° C. The RM was cooled to 20-30° C., charged with water (750 mL) and ethyl acetate (750 mL), stirred for 10-15 min. The aqueous and organic layers were separated. Aq. layer was extracted with ethyl acetate (300 mL) and stirred for 10-15 mins. The organic layer was charged with water (750 mL) and stirred for 10-15 mins. The total organic layer was cooled to 0±5° C. and stirred for 60-70 min at same temperature. The obtained solid was filtered and washed with ethyl acetate (75 mL). The wet compound was suck dried for 45-60 min at 50° C. to yield crystalline empagliflozin (HPLC purity: 99.65%)

Example 15: Preparation of Dapagliflozin (9b)

To Compound (7) (25 g), obtained from example 8, was charged acetonitrile (250 mL) in to the RB flask, followed by addition of potassium carbonate (25 g). The RM was stirred for 10 min at 20-30° C. Compound (8) (10 g), obtained from example 16, was charged to the RM, heated to 70-75° C. and stirred for 36h. After completion of the reaction, the RM was cooled to 10-15° C. Slowly water (250 mL) was added followed by addition of ethyl acetate (250 mL), stirred for 10 min. The aqueous and organic layers were separated. The organic layer was dried over anhydrous sodium sulfate and the solvent was distilled under vacuum to obtain the product as a residue (22 g), (Purity by HPLC: 99.72%).

Example 16: Preparation of Crystalline Dapagliflozin Propane-1,2-Diol

To the compound obtained from example 15, was charged (S)-1,2-propanediol (20 g). The RM was cooled to 0±5° C. Slowly cyclohexane (1.2 L) was added to the RM at same temperature over a period of 90-120 min. The RM was stirred for 60-90 min. the mass was filtered and washed with cyclohexane (360 mL). The resultant compound was dried for 10-12 hrs at 50° C. to yield crystalline dapagliflozin propane-1,2-diol. (HPLC Purity: 99.65%)

The above examples are merely illustrative, and do not limit the scope of the invention in anyway.

The foregoing embodiments and advantages are merely exemplary and are not to be construed as limiting the scope of the present invention. The description of the exemplary embodiments of the present invention is intended to be illustrative and not to limit the scope of the invention. Various modifications, alterations and variations, which are apparent to a person skilled in the art, are intended to fall within the scope of the invention.

The invention claimed is:

1. A process for the preparation of SGLT-2 inhibitors represented by a compound (9) comprising the steps of:
(a) reducing compound (1) to obtain a diphenylmethane compound (2);

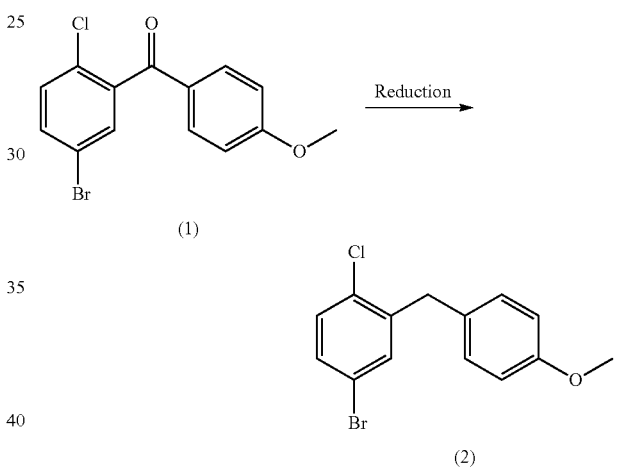

(b) coupling the diphenylmethane compound (2) with a protected gluconolactone (3) in the presence of an alkyl lithium, followed by treatment with an acid to obtain a compound (4);

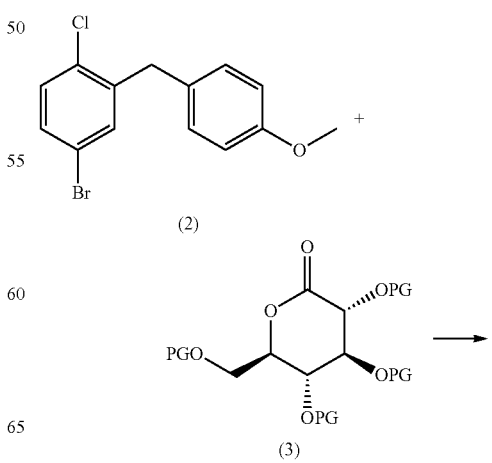

or reducing the compound (4) obtained from step (b) to obtain a compound (5a);

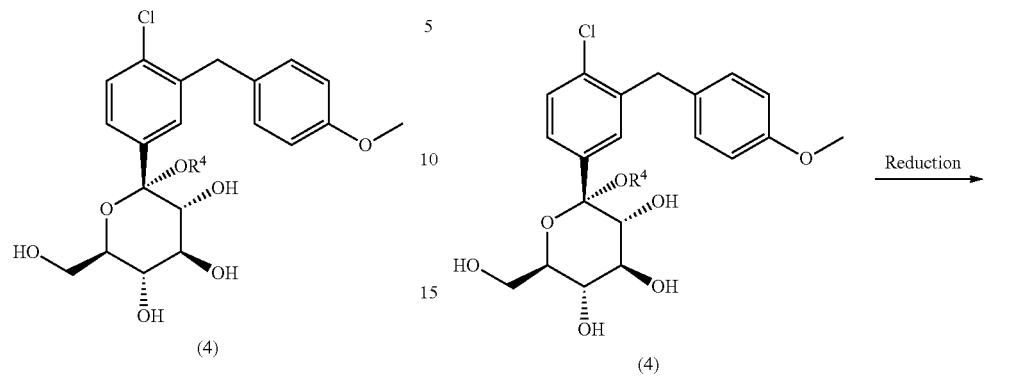

wherein in compound (3), PG is a hydroxyl protecting group selected from the group consisting of —C(O)OC$_1$-C$_6$ alkyl, optionally substituted —C(O)OC$_1$-C$_6$ aryl, optionally substituted —C$_1$-C$_{12}$ aryl(C$_1$-C$_3$)alkyl, optionally substituted C$_7$-C$_{11}$ aryl carbonyl, —C(O)C$_1$-C$_6$ alkyl, C$_1$-C$_6$ alkylsulfonyl and silyl protecting groups; R$^4$ in compound (4) is hydrogen or C$_{1-4}$ alkyl;

(c) treating the compound (4) with a suitable reagent, wherein the hydroxyl groups are protected to form a compound (5), wherein PG denotes a hydroxyl protecting group;

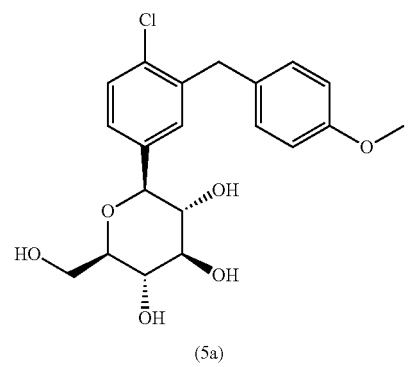

(d) reacting the compound (5) obtained from step (c) with a reducing agent to form a compound (6), wherein PG is a hydroxyl protecting group;

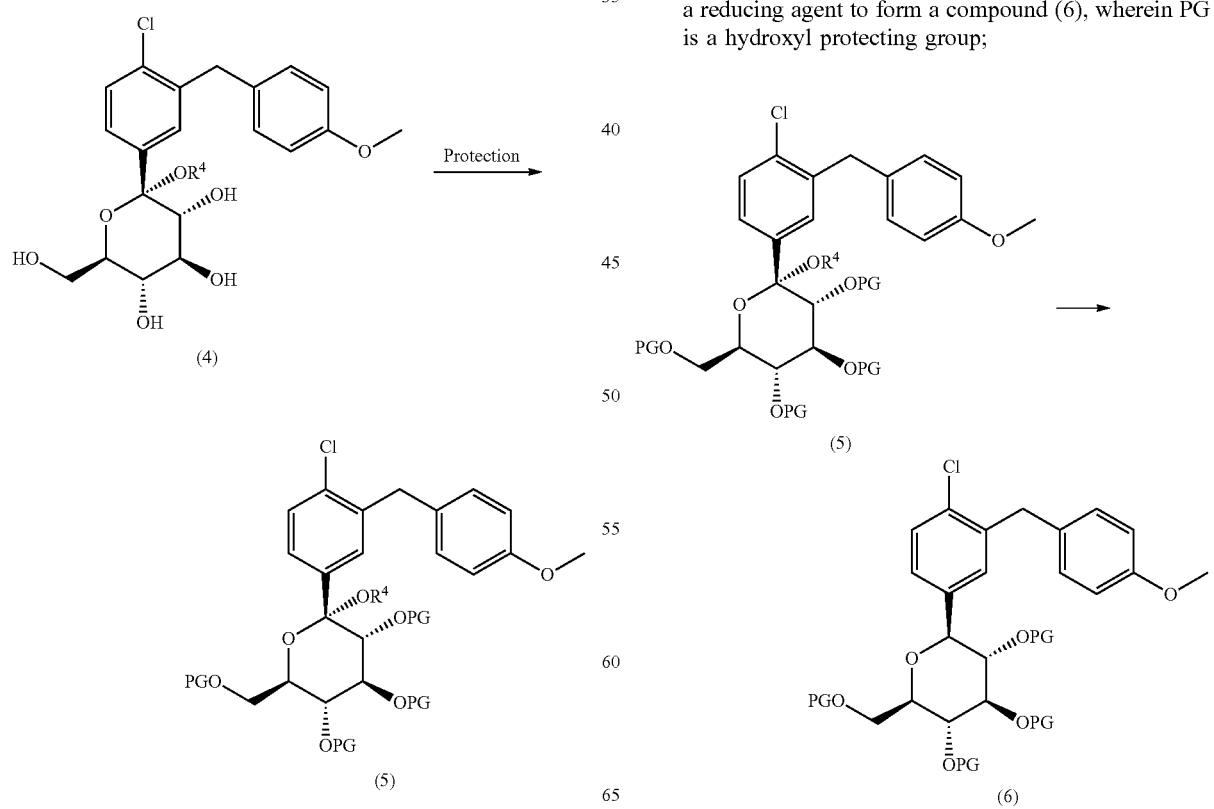

or reacting the compound (5a) obtained from step (c) with suitable reagent to protect the hydroxyl groups to form a compound (6), wherein PG is a hydroxyl protecting group;

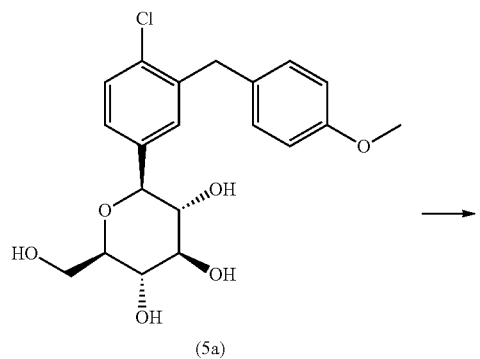

(5a)

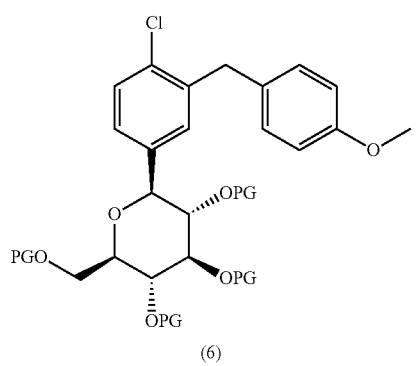

(6)

(e) subjecting the compound (6) to O-demethylation in the presence of a reagent-pair and a suitable reagent, wherein $R_1$ is hydrogen or hydroxyl protecting group (PG); and

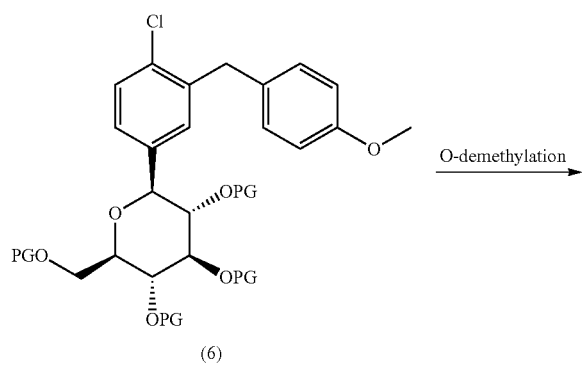

(6)

$\xrightarrow{\text{O-demethylation}}$

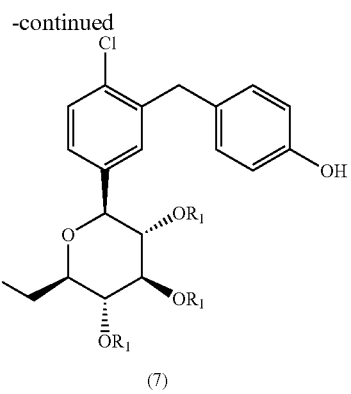

(7)

(f) reacting the compound (7) with a compound (8) in the presence of a base and optionally a phase transfer catalyst to obtain the compound (9);

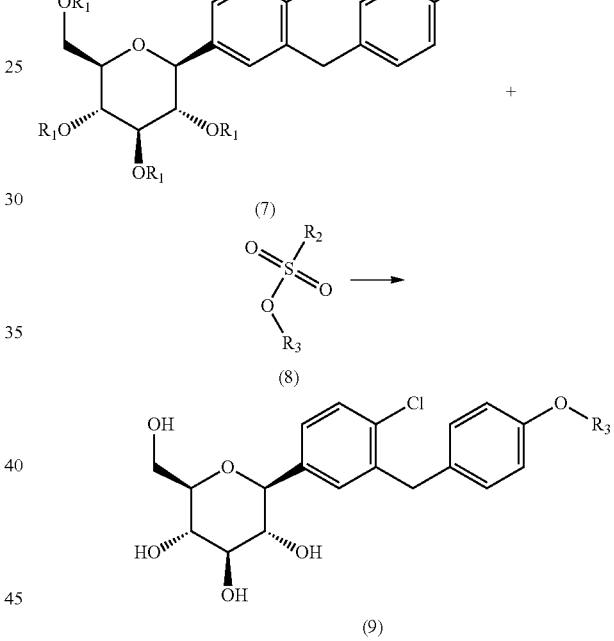

wherein $R_1$ is hydrogen or a hydroxyl protecting group; $R_2$ is trifluoromethyl, $C_{1-6}$ alkyl, or an aryl group optionally substituted at para position with halogen or $C_{1-6}$ alkyl; and $R_3$ is tetrahydrofuran-3-yl or ethyl.

2. The process as claimed in claim 1, wherein the reduction in step (a), step (c) and step (d) is carried out using silanes selected from the group consisting of triethylsilane, tripropylsilane, triisopropylsilane, and diphenylsilane; sodium borohydride, sodium cyanoborohydride, zinc borohydride, borane complexes, lithium aluminum hydride, diisobutylaluminum hydride, and vitride; Lewis acid selected from the group consisting of aluminum chloride, boron trifluoride etherate, copper (II) triflate, iron (III) chloride, tin (II) chloride, tin tetrachloride, zinc chloride, zinc iodide, indium (III) chloride, scandium triflate, trimethylsilyl triflate, and trifluoroacetic acid; or Bronsted acids selected from the group consisting of hydrochloric acid, toluenesulfonic acid, trifluoroacetic acid and acetic acid;

the coupling in step (b) is carried out using an alkyl lithium selected from the group consisting of n-, sec-, and tert-butyl lithium; the acid is selected from methanesulfonic acid, toluenesulfonic acid, hydrochloric acid, sulphuric acid, acetic acid, and ammonium chloride;

the suitable reagent in step (c) and step (d) for introducing the hydroxyl protecting group is selected from acetic anhydride, acetyl chloride, propionic anhydride, propanoyl chloride, benzoic anhydride, benzoyl chloride and 4-nitrobenzoyl chloride;

the reagent pair in step (e) is thiourea/aluminum chloride reagent pair; suitable reagent is selected from the group consisting of dodecanethiol, decanethiol, cyclohexane thiol, cyclopentane thiol, cyclobutane thiol, thiophenol, methanethiol, ethanethiol, 1-propanethiol, 2-propanethiol, n-butanethiol, tertbutanethiol, furan-2-yl methanethiol, ethanedithiol, 1,2-propanedithiol, 1,3-propanedithiol, 1,3-butanedithiol, and 1,4-butanedithiol;

the base in step (f) is an inorganic base selected from lithium hydroxide, sodium hydroxide, and potassium hydroxide; alkali metal carbonate selected from sodium carbonate, potassium carbonate, and lithium carbonate; alkali metal bicarbonate selected from sodium bicarbonate, potassium bicarbonate, lithium bicarbonate and ammonia; or an organic base selected from sodium methoxide, sodium ethoxide, sodium tertbutoxide, potassium tert-butoxide;

triethylamine, methylamine, ethylamine, 1,5-diazabicyclo (4.3.0)non-5-ene (DBN), 1,8-diazabicyclo [5 0.4 0.0] undec-7-ene (DBU), 1,4-diazabicyclo [2 0.2 0.2] octane (DABC 0), diisopropylamine, diisopropylethylamine, N-methylmorpholine, N-ethylmorpholine, piperidine, N,N-dimethylaminopyridine, pyridine, 2,6-lutidine, 2,4,6-collidine, and 1-methylimidazole, 1,2,4-triazole;

the phase transfer catalyst in step (f) is a crown ether selected from 12-crown-4, 15-crown-5 and 18-crown-6; poly(ethylene glycol) (PEG) and derivatives; or a quaternary ammonium compound selected from tetramethyl ammonium bromide, tetrabutyl ammonium bromide, tetrabutylammonium chloride methyl triethyl ammonium bromide, benzyl trimethyl ammonium bromide, and benzyl triethyl ammonium bromide.

3. The process as claimed in claim 1, wherein the process for preparing the compound (9) comprises:
(a) reacting compound (1) with sodium borohydride in the presence of aluminium chloride and tetrahydrofuran to obtain diphenylmethane compound (2);

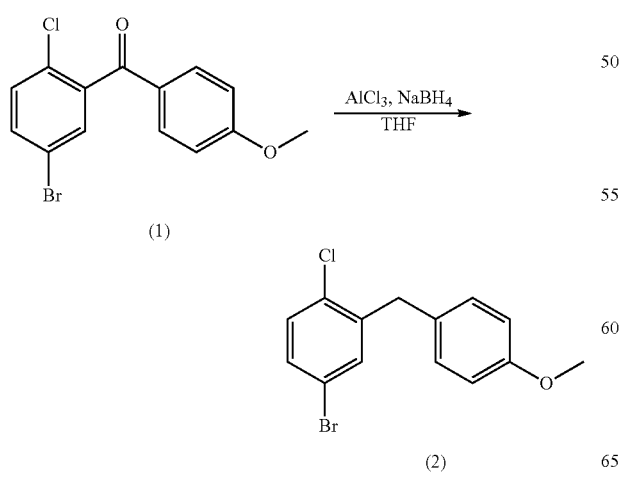

(b) coupling the diphenylmethane compound (2) with protected gluconolactone (3) in the presence of n-butyllithium and tetrahydrofuran, followed by treatment with hydrochloric acid to obtain compound (4);

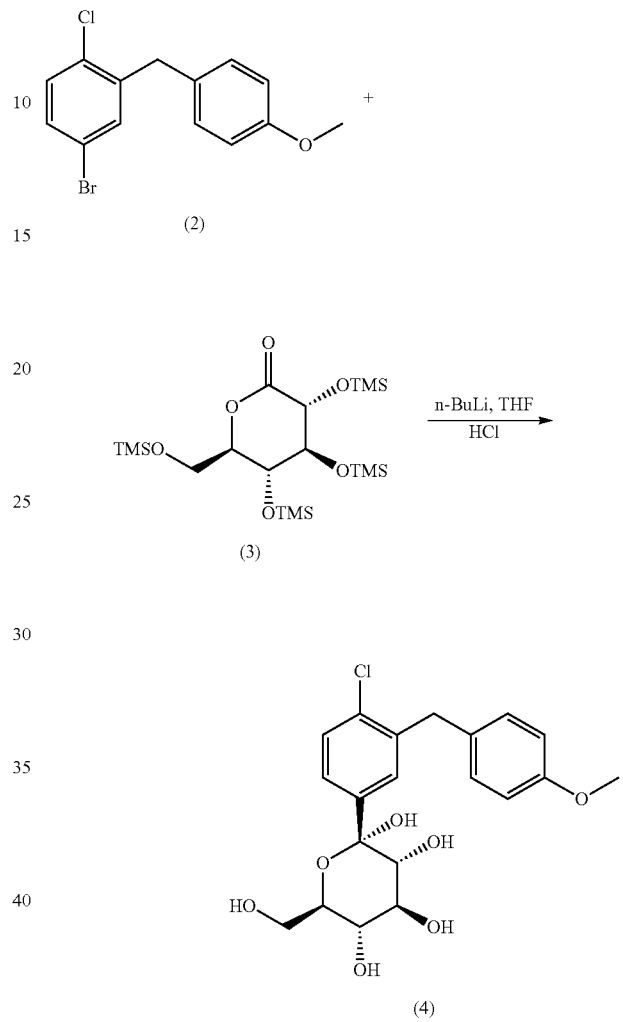

(c) reducing the compound (4) using triethylsilane and boron trifluoride etherate to obtain compound (5a);

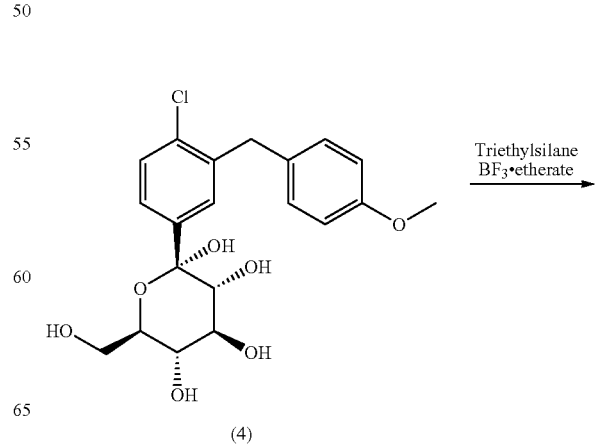

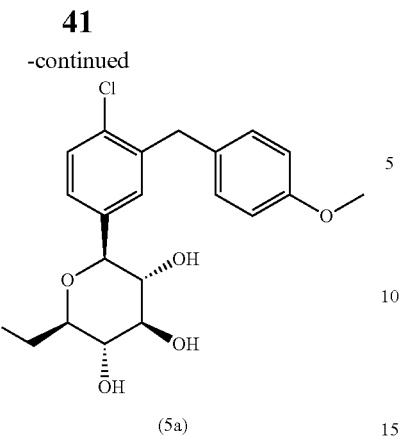

(5a)

(d) reacting the compound (5a) with acetic anhydride to protect the hydroxyl groups in the presence of N,N-dimethylaminopyridine to form compound (6);

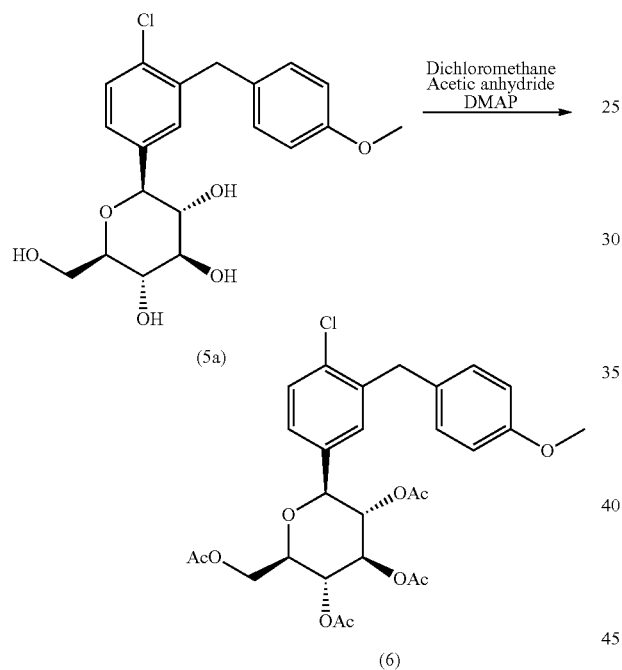

(e) subjecting the compound (6) to O-demethylation in the presence of thiourea-Aluminum aluminum chloride reagent pair and dodecanethiol to form compound (7);

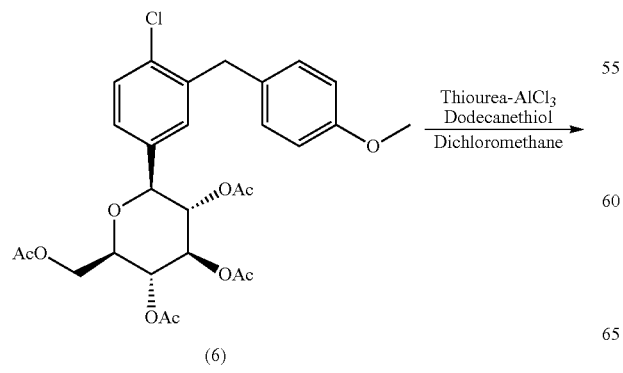

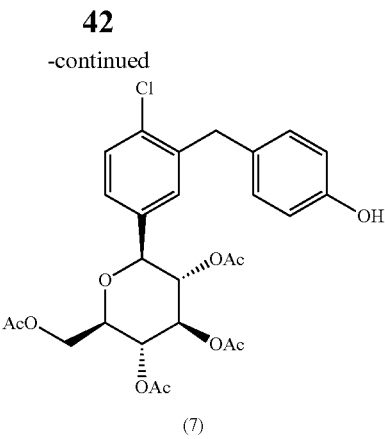

(7)

(f) reacting compound (7) with compound (8) in the presence of a base and optionally a phase transfer catalyst to obtain compound (9);

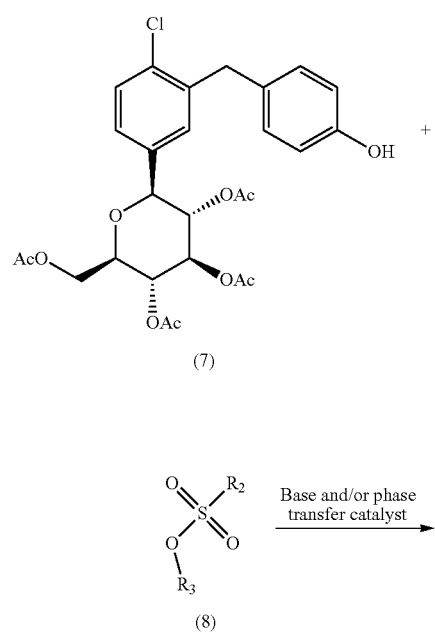

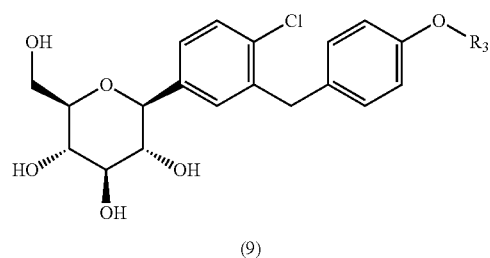

(9)

wherein $R_2$ is trifluoromethyl, $C_{1-6}$ alkyl, or an aryl group optionally substituted at para position with groups halogen, or $C_{1-6}$ alkyl; and $R_3$ is tetrahydrofuran-3-yl or ethyl.

4. The process as claimed in claim 1, wherein the process for preparing the compound (9) comprises:

(a) reacting compound (1) with sodium borohydride in the presence of aluminium chloride and tetrahydrofuran to obtain diphenylmethane compound (2);

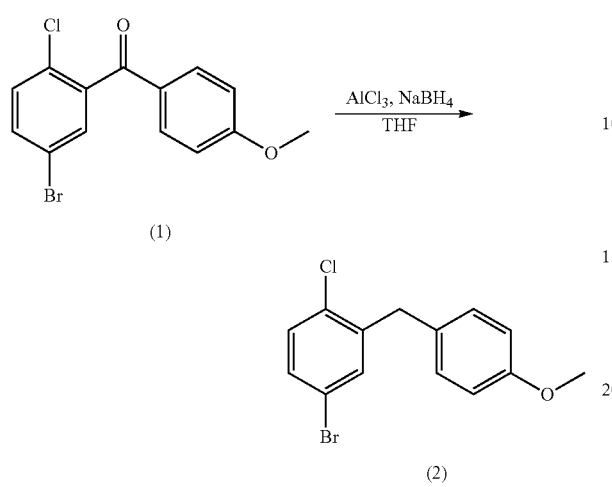

(b) coupling the diphenylmethane compound (2) with protected gluconolactone (3) in the presence of n-butyl-lithium and tetrahydrofuran, followed by treatment with methanesulfonic acid in methanol to obtain compound (4);

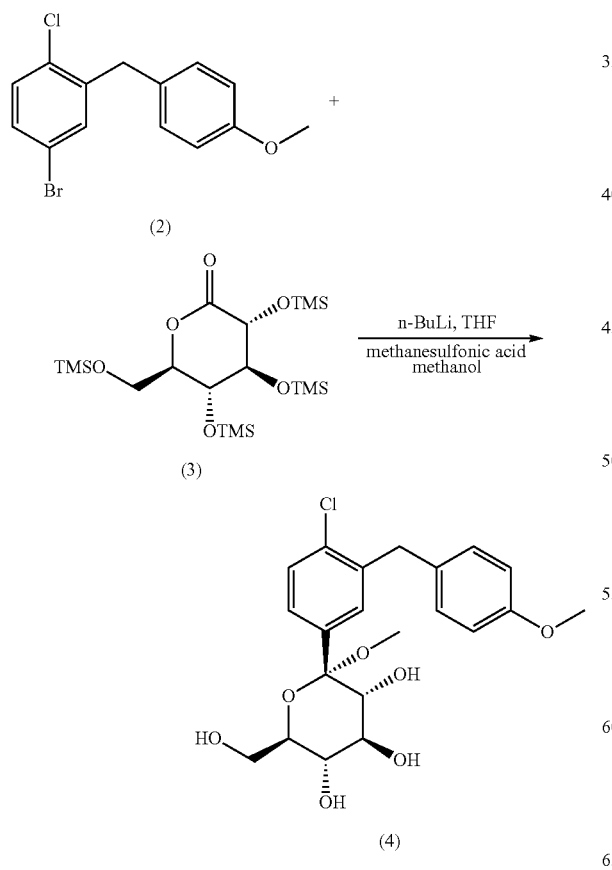

(c) reducing the compound (4) using triethylsilane and boron trifluoride etherate to obtain compound (5a);

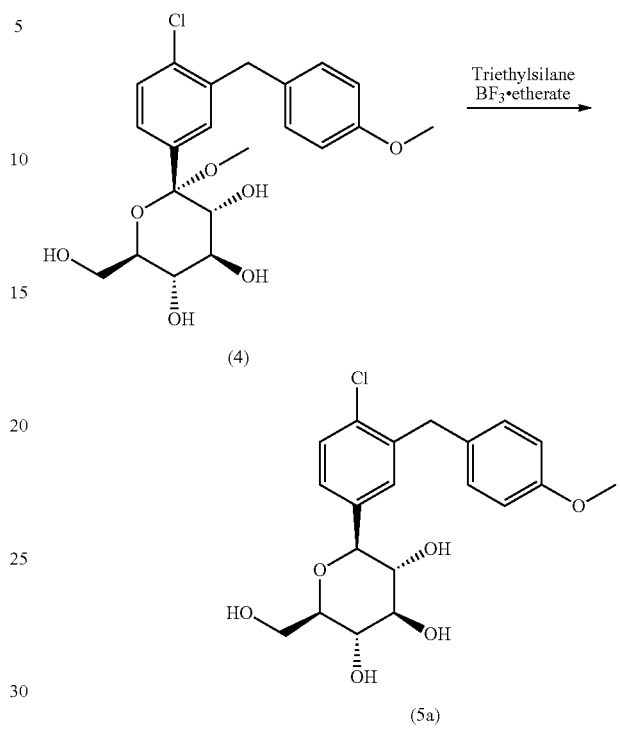

(d) reacting the compound (5a) with acetic anhydride to protect the hydroxy groups in the presence of N,N-dimethylaminopyridine to form compound (6);

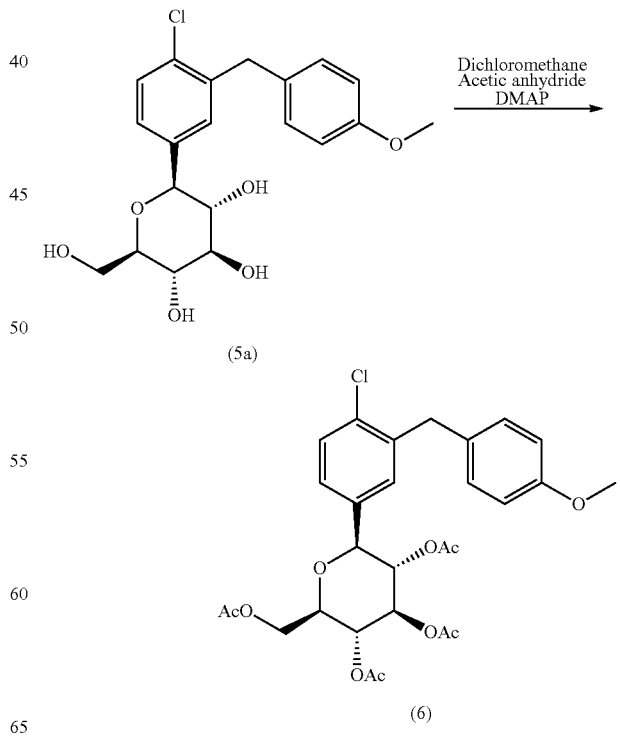

(e) subjecting the compound (6) to O-demethylation in the presence of thiourea aluminum chloride reagent pair and dodecanethiol to form compound (7);

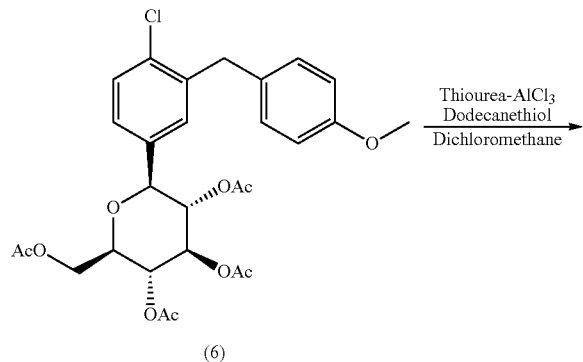

(6)

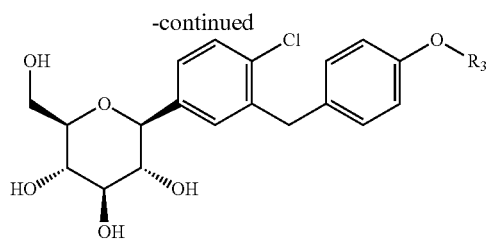

(9)

wherein $R_2$ is trifluoromethyl, $C_{1-6}$ alkyl, or an aryl group optionally substituted at para position with groups halogen, or $C_{1-6}$ alkyl; and $R_3$ is tetrahydrofuran-3-yl or ethyl.

5. The process as claimed in claim 1, wherein the compound (9) is (1S)-1,5-anhydro-1-C-P-chloro-3-[(4-ethoxyphenyl)methyl] phenyl]-D-glucitol, dapagliflozin (compound 9b) and the process for preparing the compound 9b comprises reacting compound (7) with compound (8) in the presence of a base and optionally a phase transfer catalyst;

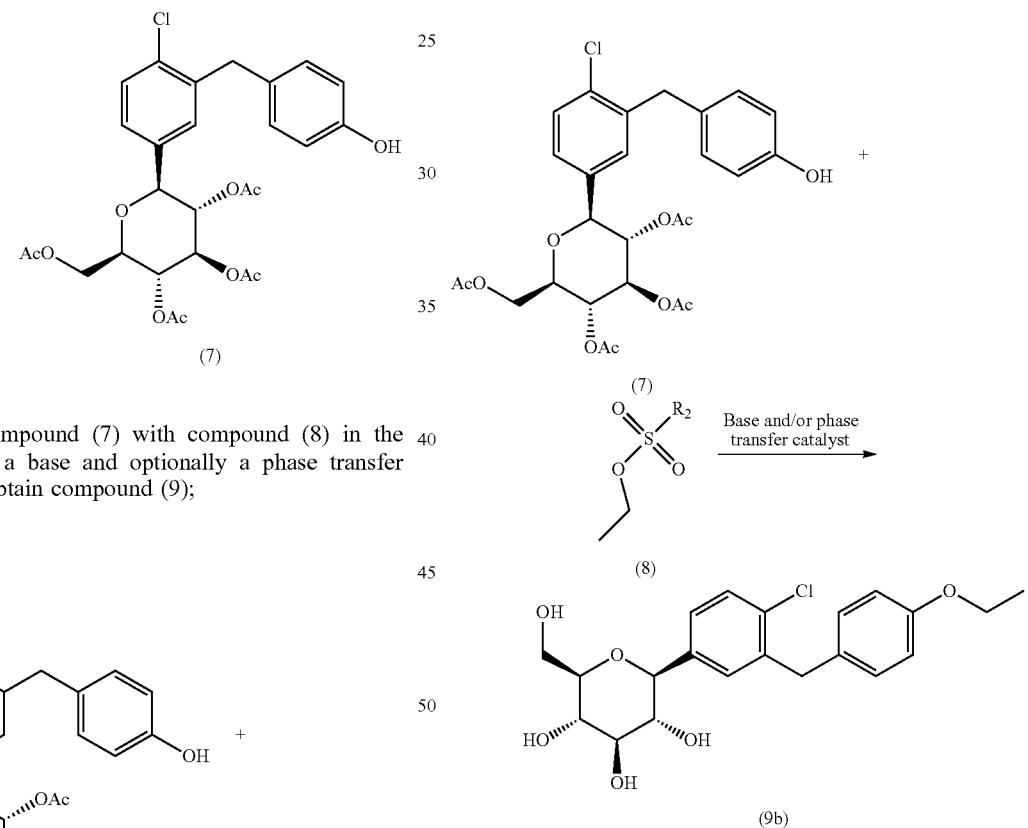

(f) reacting compound (7) with compound (8) in the presence of a base and optionally a phase transfer catalyst to obtain compound (9);

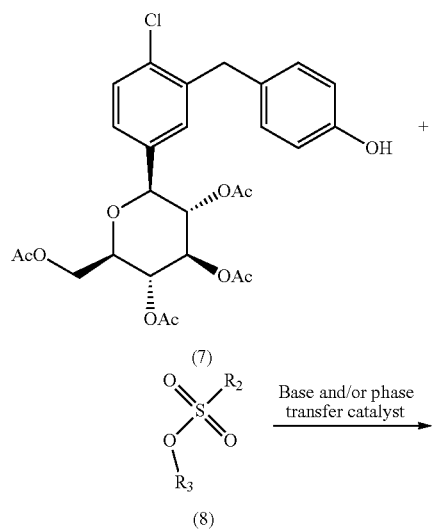

wherein $R_2$ is trifluoromethyl, $C_{1-6}$ alkyl, or an aryl group optionally substituted at para position with halogen or $C_{1-6}$ alkyl; the base is selected from the group consisting of sodium hydroxide, potassium hydroxide, sodium carbonate and potassium carbonate; and the phase transfer catalyst is selected from 18-crown-6, poly(ethylene glycol) and tetrabutyl ammonium bromide.

6. The process as claimed in claim 5, wherein the process further comprises:
(a) dissolving dapagliflozin in one or more solvents;
(b) cooling the reaction mass to a suitable temperature;

(c) adding propane-1,2-diol to the reaction mixture of step (b);

(d) stirring, filtering and removing the solvent followed by drying to isolate crystalline dapagliflozin propane-1,2-diol;

wherein the solvent is a hydrocarbon solvent selected from n-hexane, n-heptane, cyclohexane, toluene, pentane, cycloheptane, methylcyclohexane, ethyl benzene and o-, m- or p-xylenes; ether solvent selected from 1,2-dimethoxyethane, tetrahydrofuran, 1,4-dioxane, diethyl ether, ethylene glycol dimethyl ether, ethylene glycol diethyl ether, diethylene glycol dimethyl ether, diethylene glycol diethyl ether, triethylene glycol dimethyl ether, t-butyl methyl ether and diisopropyl ether; ester solvent selected from ethyl formate, methyl acetate, ethyl acetate, isopropyl acetate, n-butyl acetate, t-butyl acetate, and isobutyl acetate; polar aprotic solvent selected from N,N-dimethylacetamide (DMA), N,N-dimethylformamide (DMF), dimethylsulfoxide (DMSO), and N-methylpyrrolidone (NMP); chlorinated solvent selected from dichloromethane, and chloroform; ketone solvent selected from acetone, methyl ethyl ketone, 2-pentanone, 3-pentanone, methyl butyl ketone and methyl isobutyl ketone; nitrile solvent selected from acetonitrile; alcoholic solvents selected from methanol, ethanol, n-propanol, isopropanol, n-butanol, isobutanol, t-butanol, 2-fluoroethanol, 2,2,2-trifluoroethanol, ethylene glycol, 2-methoxyethanol, 2-ethoxyethanol, diethylene glycol, diethylene glycol mono methyl ether, and cyclohexanol; or water.

7. The process as claimed in claim 1, wherein the compound (9) is (1S)- 1,5-anhydro- 1-C- [4-chloro-3- [ [4- [ [(3S)-tetrahydro-3-furanyl] oxy]phenyl]methyl]phenyl]-D-glucitol, empagliflozin (compound 9a) and the process for preparing the compound 9a comprises reacting compound (7) with compound (8) in the presence of a base and optionally a phase transfer catalyst;

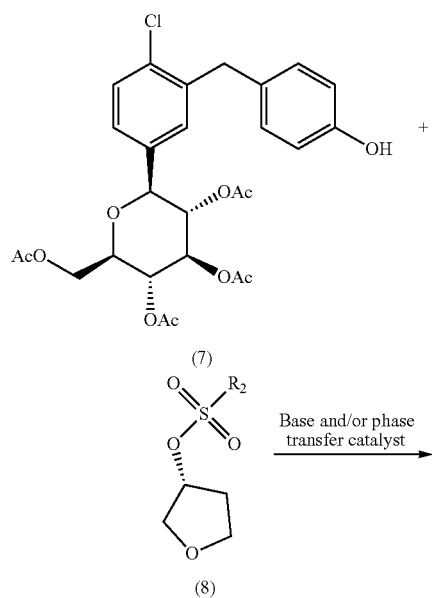

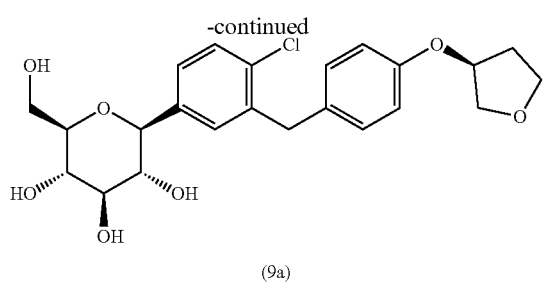

wherein $R_2$ is trifluoromethyl, $C_{1-6}$ alkyl, or an aryl group optionally substituted at para position with halogen or $C_{1-6}$ alkyl; the base is selected from the group consisting of sodium hydroxide, potassium hydroxide, sodium carbonate and potassium carbonate; and the phase transfer catalyst is selected from 18-crown-6, poly (ethylene glycol) and tetrabutyl ammonium bromide.

8. The process as claimed in claim 7, wherein the process further comprises:
(a) dissolving empagliflozin in a solvent or a mixture of solvents;
(b) heating and stirring the reaction mixture to a suitable temperature to form a clear solution;
(c) cooling the reaction mixture;
(d) filtering the solution, followed by drying to provide crystalline empagliflozin;

wherein the solvent is a hydrocarbon solvent selected from n-hexane, n-heptane, cyclohexane, toluene, pentane, cycloheptane, methylcyclohexane, ethyl benzene and o-, m- or p-xylenes; ether solvent selected from 1,2-dimethoxyethane, tetrahydrofuran, 1,4-dioxane, diethyl ether, ethylene glycol dimethyl ether, ethylene glycol diethyl ether, diethylene glycol dimethyl ether, diethylene glycol diethyl ether, triethylene glycol dimethyl ether, t-butyl methyl ether and diisopropyl ether; ester solvent selected from ethyl formate, methyl acetate, ethyl acetate, isopropyl acetate, n-butyl acetate, t-butyl acetate, and isobutyl acetate; polar aprotic solvent selected from N,N-dimethylacetamide (DMA), N,N-dimethylformamide (DMF), dimethylsulfoxide (DMSO), and N-methylpyrrolidone (NMP); chlorinated solvent selected from dichloromethane, and chloroform; ketone solvent selected from acetone, methyl ethyl ketone, 2-pentanone, 3-pentanone, methyl butyl ketone and methyl isobutyl ketone; nitrile solvent selected from acetonitrile; alcoholic solvents selected from methanol, ethanol, n-propanol, isopropanol, n-butanol, isobutanol, t-butanol, 2-fluoroethanol, 2,2,2-trifluoroethanol, ethylene glycol, 2-methoxyethanol, 2-ethoxyethanol, diethylene glycol, diethylene glycol mono methyl ether, and cyclohexanol; or water.

9. The process as claimed in claim 7, wherein the process further comprises:
(a) dissolving empagliflozin in one or more solvents;
(b) optionally filtering the undissolved particles;
(c) distilling the solvent completely; and
(d) drying to isolate an amorphous empagliflozin;

wherein the solvent is a hydrocarbon solvent selected from n-hexane, n-heptane, cyclohexane, toluene, pentane, cycloheptane, methylcyclohexane, ethyl benzene and o-, m- or p-xylenes; ether solvent selected from 1,2-dimethoxyethane, tetrahydrofuran, 1,4-dioxane, diethyl ether, ethylene glycol dimethyl ether, ethylene glycol diethyl ether, diethylene glycol dimethyl ether, diethylene glycol diethyl ether, triethylene glycol dimethyl ether, t-butyl methyl ether and diisopropyl ether; ester solvent selected from ethyl formate, methyl acetate, ethyl acetate, isopropyl acetate, n-butyl acetate, t-butyl acetate, and isobutyl acetate; polar aprotic solvent selected from N,N-dimethylacetamide (DMA), N,N-dimethylformamide (DMF), dimethylsulfoxide (DMSO), and N-methylpyrrolidone (NMP); chlorinated solvent selected from dichloromethane, and chloroform; ketone solvent selected from acetone, methyl ethyl ketone, 2-pentanone, 3-pentanone, methyl butyl ketone and methyl isobutyl ketone; nitrile solvent selected from acetonitrile; alcoholic solvents selected from methanol, ethanol, n-propanol, isopropanol, n-butanol, isobutanol, t-butanol, 2-fluoroethanol, 2,2,2-trifluoroethanol, ethylene glycol, 2-methoxyethanol, 2-ethoxyethanol, diethylene glycol, diethylene glycol mono methyl ether, and cyclohexanol; or water.

\* \* \* \* \*